(12) United States Patent
Cooper et al.

(10) Patent No.: US 9,907,820 B2
(45) Date of Patent: Mar. 6, 2018

(54) POLYCLONAL GAMMA DELTA T CELLS FOR IMMUNOTHERAPY

(71) Applicant: BOARD OF REGENTS, THE UNIVERSITY OF TEXAS SYSTEM, Austin, TX (US)

(72) Inventors: Laurence J. N. Cooper, Houston, TX (US); Drew C. Deniger, Germantown, MD (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 15/031,610

(22) PCT Filed: Oct. 24, 2014

(86) PCT No.: PCT/US2014/062191
§ 371 (c)(1),
(2) Date: Apr. 22, 2016

(87) PCT Pub. No.: WO2015/061694
PCT Pub. Date: Apr. 30, 2015

(65) Prior Publication Data
US 2016/0256487 A1 Sep. 8, 2016

Related U.S. Application Data

(60) Provisional application No. 61/895,626, filed on Oct. 25, 2013.

(51) Int. Cl.
*C12N 5/0783* (2010.01)
*A61K 35/17* (2015.01)
*A61K 39/00* (2006.01)

(52) U.S. Cl.
CPC .......... *A61K 35/17* (2013.01); *A61K 39/0011* (2013.01); *C12N 5/0636* (2013.01); *C12N 5/0638* (2013.01); *A61K 2039/5158* (2013.01); *A61K 2039/572* (2013.01); *C12N 2501/2302* (2013.01); *C12N 2501/2321* (2013.01); *C12N 2501/515* (2013.01); *C12N 2502/11* (2013.01); *C12N 2502/99* (2013.01)

(58) Field of Classification Search
None
See application file for complete search history.

(56) References Cited

U.S. PATENT DOCUMENTS

| | | | |
|---|---|---|---|
| 7,638,325 | B2 | 12/2009 | June et al. |
| 2011/0236363 | A1 | 9/2011 | Chang et al. |
| 2012/0107292 | A1 | 5/2012 | Nieda et al. |
| 2012/0321666 | A1 | 12/2012 | Cooper et al. |

FOREIGN PATENT DOCUMENTS

| | | |
|---|---|---|
| WO | WO 97/32970 | 9/1997 |
| WO | WO 2005/118788 | 12/2005 |
| WO | WO 2008/045286 | 4/2008 |
| WO | WO 2012/156958 | 11/2012 |
| WO | WO2012/156958 A2 * | 11/2012 |
| WO | WO 2013/074916 | 5/2013 |

OTHER PUBLICATIONS

Deniger D.C. (T-cell Treatments for Solid and Hematological Tumors, 8/13, 1-278).*
ReportsWeb (2016).*
Deniger et al., "Specificity of human gamma delta T cells can be re-directed to CD19 while avoiding unwanted allogeneic responses", *Poster Abstract 41—Society for Immunotherapy of Cancer 26th Annual Meeting*, Nov. 2011.
Deniger et al., "Specificity of human gamma delta T cells can be re-directed to CD19 while avoiding unwanted allogeneic responses", *Poster—Society for Immunotherapy of Cancer 26th Annual Meeting*, Nov. 2011.
Deniger et al., Activating and propagating polyclonal gamma delta T cells with broad specificity for malignancies. Clin Cancer Res. Nov. 15, 2014;20(22):5708-19. doi: 10.1158/1078-0432.CCR-13-3451. Epub May 15, 2014.
Deniger et al., Bispecific T-cells expressing polyclonal repertoire of endogenous γδ T-cell receptors and introduced CD19-specific chimeric antigen receptor. Mol Ther. Mar. 2013;21(3):638-47. doi: 10.1038/mt.2012.267. Epub Jan. 8, 2013.
Deniger et al., Clinical applications of gamma delta T cells with multivalent immunity. Front Immunol. Dec. 11, 2014;5:636. doi: 10.3389/fimmu.2014.00636. eCollection 2014.
Deniger, "T-Cell treatments for solid and hematological tumors", *UT GBS Dissertations and Theses*, dated Aug. 2013, retrieved from digitalcommons.library.tmc.edu/cgi/viewcontent.cgi?article=1421 &context=utgsbs_dissertations on Dec. 14, 2014.
PCT International Preliminary Report on Patentability issued in International Application No. PCT/US2014/062191, dated Apr. 26, 2016.
PCT International Search Report and Written Opinion issued in International Application No. PCT/US2014/062191, dated Apr. 22, 2015.
Correia et al., "Differentiation of human peripheral blood Vδ1+ T cells expressing the natural cytotoxicity receptor NKp30 for recognition of lymphoid leukemia cells." Blood 118.4 (2011): 992-1001.
Invitation to Pay Additional Fees and Partial Supplemental European Search Report issued in European Application No. 14854993.4, dated May 30, 2017.
Extended European Search Report issued in European Application No. 14854993.4, dated Oct. 5, 2017.
Huarte et al. "Ex vivo expansion of tumor specific lymphocytes with IL-15 and IL-21 for adoptive immunotherapy in melanoma." *Cancer letters* 285.1 (2009): 80-88.
Santegoets et al. "IL-21 promotes the expansion of CD27+ CD28+ tumor infiltrating lymphocytes with high cytotoxic potential and low collateral expansion of regulatory T cells." *Journal of translational medicine* 11.1 (2013): 37.

* cited by examiner

*Primary Examiner* — Michael Szperka
*Assistant Examiner* — Marianne DiBrino
(74) *Attorney, Agent, or Firm* — Parker Highlander PLLC

(57) ABSTRACT

Provided herein is a method of expanding clinically-relevant quantities of polyclonal γδ T cells that have anti-tumor, anti-viral, and anti-bacterial reactivity. Polyclonal γδ T cells can target a variety of tumors, including solid tumors as well as other conditions, such as viral and bacterial infections.

7 Claims, 22 Drawing Sheets

POLYCLONAL GAMMA DELTA T CELLS FOR IMMUNOTHERAPY

This application is a national phase application under 35 U.S.C. § 371 of International Application No. PCT/US2014/062191, filed Oct. 24, 2014, which claims the priority benefit of U.S. Provisional Patent Application No. 61/895,626, filed Oct. 25, 2013, the entire contents of which are incorporated herein by reference.

The invention was made with government support under Grant No. 10626252 awarded by the Department of Defense. The government has certain rights in the invention.

BACKGROUND OF THE INVENTION

1. Field of the Invention

The present invention relates generally to the fields of medicine and immunology. In certain aspects, the field of the invention concerns immunotherapy. More particularly, it concerns the manufacture of clinical-grade polyclonal γδ T cells and therapeutic methods using such cells.

2. Description of Related Art

Human γδ T cells have both innate and adaptive qualities exhibiting a range of effector functions, including cytolysis upon cell contact (Bonneville et al., 2010). Recognition and subsequent killing of tumor target cells is achieved by heterodimers of γ and δ T-cell receptor (TCR) chains. The human TCR variable (V) region defines 14 unique Vγ alleles, 3 unique Vδ alleles (Vδ1, Vδ2, and Vδ3), and 5 Vδ alleles that share a common nomenclature with Vα alleles (Vδ4/Vα14, Vδ5/Vα29, Vδ6/Vα23, Vδ7/Vα36, and Vδ8/Vα38-2) (Lefranc, 2001). T cells expressing TCRα/TCRβ heterodimers compose approximately 95% of peripheral blood (PB) T cells and recognize peptides in the context of major histocompatibility complex (MHC) molecules (Turchinovich and Pennington, 2011). In contrast, TCRγδ ligands are recognized independent of MHC restriction but are infrequent (1%-5% of T cells) in PB (Bonneville et al., 2010; Kabelitz et al., 2007; Xu et al., 2011).

Human γδ T cells exhibit an inherent ability to lyse tumor cells and hold promise for immunotherapy. As such, many TCRγδ ligands are present on cancer cells, raising the possibility that an expansion approach that maintains a polyclonal repertoire of γδ TCRs has appeal for human application. Adoptive transfer of Vγ9Vδ2 T cells has yielded objective clinical responses for investigational treatment of cancer, but administration of non-Vγ9Vδ2 T cells has yet to be performed (Kondo et al., 2008; Lang et al., 2011; Nagamine et al., 2009; Nicol et al., 2011; Wilhelm et al., 2003). Long-term remissions of leukemia among recipients of haploidentical αβ T cell-depleted hematopoietic stem cell transplant (HSCT) correlated with increased engraftment frequency of donor-derived Vδ1 T cells (Godder et al., 2007; Lamb et al., 1999; Lamb et al., 1996; Lamb et al., 2001). No reports to date have described the therapeutic impact of Vδ1$^{neg}$Vδ2$^{neg}$ T cells and this subset has not been directly compared to T cells expressing Vδ1 and Vδ2 TCRs. Thus, there are significant gaps in the knowledge and human application of non-Vγ9Vδ2 lineages.

Aminobisphosphonates, e.g., zoledronic acid (Zol), have been used to propagate the Vγ9Vδ2 subset of γδ T cells for clinical use (Stresing et al., 2007; Thompson et al., 2010). Other γδ T cell lineages are not propagated by aminobisphosphonates. Nonetheless, clinical trials that have used Vγ9Vδ2 γδ T cells as cancer immunotherapies have shown some objective responses but were not curative as a single therapy (Nicol et al., 2011; Wilhelm et al., 2003). Plate-bound antibodies and cytokine cocktails have also been used to propagate a more diverse set of γδ T cells, but (i) they did not achieve consistent Vδ1 and Vδ1$^{neg}$Vδ2$^{neg}$ frequencies, (ii) the absolute numbers of γδ T cells were not clinically-relevant (<10$^8$ cells), (iii) they did not comprehensively analyze Vγ frequencies, and (iv) they are not as directly translatable to the clinic as these reagents are not all available at good manufacturing practices (GMP) quality (Dokouhaki et al., 2010; Kang et al., 2009; Lopez et al., 2000). Therefore, clinically-relevant methods of expanding γδ T cells ex vivo, and the cells produced thereby, are greatly needed.

SUMMARY OF THE INVENTION

Provided herein is a method of expanding clinically-relevant quantities of polyclonal γδ T cells that have anti-tumor, anti-viral, and anti-bacterial reactivity. γδ T cells can target a variety of tumors, including solid tumors as well as other conditions, such as viral and bacterial infections.

In one embodiment, a cell composition is provided comprising at least about 10$^9$ purified γδ T cells. The cell composition may comprise at least about 10$^9$, 10$^{10}$, 10$^{11}$ or more purified γδ T cells. In one aspect, the purified γδ T cells may be of the Vδ1, Vδ2, and Vδ1$^{neg}$Vδ2$^{neg}$ TCR subsets. In one aspect, the purified γδ T cells may express any combination of a Vδ1, Vδ2, Vδ3, Vδ5, Vδ7, or Vδ8 TCR chain with a Vγ2, Vγ3, Vγ7, Vγ8, Vγ9, Vγ10, or Vγ11 TCR chain. In one aspect, the purified γδ T cells may have essentially identical genetic material. In one aspect, the purified γδ T cells may not contain a chimeric antigen receptor.

In one aspect, the cell composition may not contain NK cells or αβ T cells. In one aspect, the γδ T cells may express CD3. In further aspects, the γδ T cells may express or co-express CD38, CD95, CD25, CD27, CD28, CD45, or CCR7. In one aspect, the γδ T cells may not express CXCR4, CCR4, CLA, CD4, CD8, CD122, CD127, CD56, CD57, or PD-1.

In various aspects, γδ T cells of the present embodiment may be genetically edited to improve therapeutic potential. Such genetic editing may be performed by any means known in the art, such as, for example, by the use of artificial nuclease(s). Such genetic editing may redirect the specificity of the γδ T cells through the expression of a chimeric antigen receptor (CAR) or T-cell receptor (TCR). Such genetic editing may improve the potency of the γδ T cells by improving homing, cytokine production, recycle killing, and/or improved engraftment.

In one embodiment, a pharmaceutical composition is provided comprising a cell composition of the present embodiments and a pharmaceutically acceptable carrier.

In one embodiment, a method of producing a cell composition of the present embodiments is provided. The method may comprise obtaining a sample of cells comprising a first polyclonal γδ T-cell population; and culturing the first polyclonal γδ T-cell population with artificial antigen presenting cells (aAPCs) in the presence of interleukin-2 (IL-2) and interleukin-21 (IL-21). In some aspects, the culturing may occur ex vivo for a limited period of time in order to expand the T-cell population. In one aspect, the culturing step may further comprise culturing with an aminobisphosphonate (e.g., zoledronic acid).

In one aspect, the sample of cells may be a peripheral blood sample or an umbilical cord blood sample. In another aspect, the sample of cells may be obtained from tissues. In another aspect, the sample of cells may be obtained from a single subject. The subject may be a donor or a patient. In some aspects, γδ T cells generated from a single donor may be infused into one or more allogeneic recipients. In one aspect, the γδ T cells may be human γδ T cells.

In some aspects, purification of the initial population of γδ T cells prior to culturing may comprise isolation/enrichment, such as with paramagnetic bead selection or flow cytometry. Such selection may comprise depleting the sample of cells of CD56- and TCRαβ-expressing cells. The purity of the γδ T cells may be based on the presence of TCR that stains with a monoclonal antibody specific for one or more γδ TCR.

In one aspect, the aAPCs may be transgenic K562 cells. In one aspect, the aAPCs may express CD137L. In other aspects, the aAPCs may further express CD19, CD64, CD86, or mIL15. In certain aspects, the aAPCs may expression at least one anti-CD3 antibody clone, such as, for example, OKT3 and/or UCHT1. In one aspect, the aAPCs may be inactivated (e.g., irradiated). In one aspect, the aAPCs may have been tested for and confirmed to be free of infectious material. Methods for producing such aAPCs are known in the art.

In one aspect, the first polyclonal γδ T-cell population may comprise about $10^4$ to about $10^6$ γδ T cells. In one aspect, culturing the first polyclonal γδ T-cell population with aAPCs may comprise culturing the cells at a ratio of about 10:1 to about 1:10; about 3:1 to about 1:5; about 1:1 to about 1:3 (γδ T cells to aAPCs); or any range derivable therein. For example, the co-culture of T cells and aAPCs can be at a ratio of about 1:1, about 1:2 or about 1:3.

In one aspect, the aAPC in the culture may be replenished every week. In one aspect, culturing the first polyclonal γδ T cell population with aAPCs may comprise culturing for at least two weeks. In one aspect, culturing the first polyclonal γδ T-cell population with aAPCs may result in at least a 100-fold increase in the number of polyclonal γδ T cells.

In one embodiment, a method of producing a cell composition of the present embodiments is provided. The method may comprise obtaining a sample of cells comprising a first polyclonal γδ T-cell population; and culturing the first polyclonal γδ T-cell population in the presence of at least one anti-CD3 antibody clone, such as, for example, OKT3 and/or UCHT1, and further in the presence of interleukin-2 (IL-2) and interleukin-21 (IL-21). In some aspects, the anti-CD3 antibody clone may be expressed on the surface of an aAPC. In other aspects, the anti-CD3 antibody clone may be on the surface of a microbead.

In some aspects, the culturing may occur ex vivo for a limited period of time in order to expand the T-cell population. In one aspect, the culturing step may further comprise culturing with an aminobisphosphonate (e.g., zoledronic acid).

In one aspect, the sample of cells may be a peripheral blood sample or an umbilical cord blood sample. In another aspect, the sample of cells may be obtained from a single subject. The subject may be a donor or a patient. In one aspect, the γδ T cells may be human γδ T cells. In some aspects, the γδ T cells may be derived from stem cells, such as embryonic stem cells, hematopoietic stem cells, or induced pluripotent stem cells.

In some aspects, purification of the initial population of γδ T cells prior to culturing may comprise paramagnetic bead selection or flow cytometry. Such selection may comprise depleting the sample of cells of CD56- and TCRαβ-expressing cells. The purity of the γδ T cells may be based on the presence of TCR that stains with a monoclonal antibody specific for the γδ TCR and absence of staining for αβ TCR.

In one aspect, culturing the first polyclonal γδ T cell population with aAPCs may comprise culturing for at least two weeks. In one aspect, culturing the first polyclonal γδ T-cell population may result in at least a 100-fold increase in the number of polyclonal γδ T cells.

In one embodiment, a method of treating a disease in a patient is provided comprising administering an effective amount of a cell composition or a pharmaceutical composition of the present embodiments. In one aspect, the patients may be a human patient.

In one aspect, the disease may be cancer. In certain aspects, the cancer may be a hematological or solid cancer, such as T-cell ALL, B-ALL, CML, colon cancer, ovarian cancer, neuroblastoma, brain tumor(s), or pancreatic cancer. In some aspects, the patient may have undergone a previous anti-cancer therapy. In one aspect, the patient may be in remission. In yet another aspect, the patient may be free of symptoms of the cancer but comprise detectable cancer cells.

In another aspect, the disease may be a viral infection (e.g., cytomegalovirus (CMV), Epstein-Barr virus (EBV), or human immunodeficiency virus (HIV)). In yet another aspect, the disease may be a bacterial infection. In one aspect, the disease may be sepsis.

In one aspect, the cell composition may be allogeneic to the patient. In various aspects, an allogeneic cell composition may or may not share HLA with the patient. In another aspect, the cell composition may be autologous to the patient.

In one embodiment, a method of treating a disease in a patient is provided comprising producing a cell composition according to the methods of the present embodiments and administering an effective amount of said cell composition to a patient in need thereof.

In some aspects, methods are provided for treating an individual with a medical condition comprising the step of providing an effective amount of cells from the population of cells described herein, including more than once in some aspects, such as at least 1, 2, 3, 4, 5, 6, 7, 8, 9, 10, 11, 12, 13, 14, or more days apart.

In one embodiment, a composition comprising a cell population or pharmaceutical composition of the present embodiments is provided for use in the treatment of a disease in a patient. The disease may be a cancer (e.g., T-cell ALL, B-ALL, AML, colon cancer, ovarian cancer, pancreatic cancer, etc.), a viral infection (e.g., cytomegalovirus (CMV), Epstein-Barr virus (EBV), or human immunodeficiency virus (HIV)), or a bacterial infection (e.g., sepsis). In one aspect, the cell composition may be allogeneic to the patient. In another aspect, the cell composition may be autologous to the patient. In another embodiment, the use of a cell population of the present embodiments in the manufacture of a medicament for the treatment of a disease is provided.

Embodiments discussed in the context of methods and/or compositions of the invention may be employed with respect to any other method or composition described herein. Thus, and embodiment pertaining to one method or composition may be applied to other methods and compositions of the invention as well.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
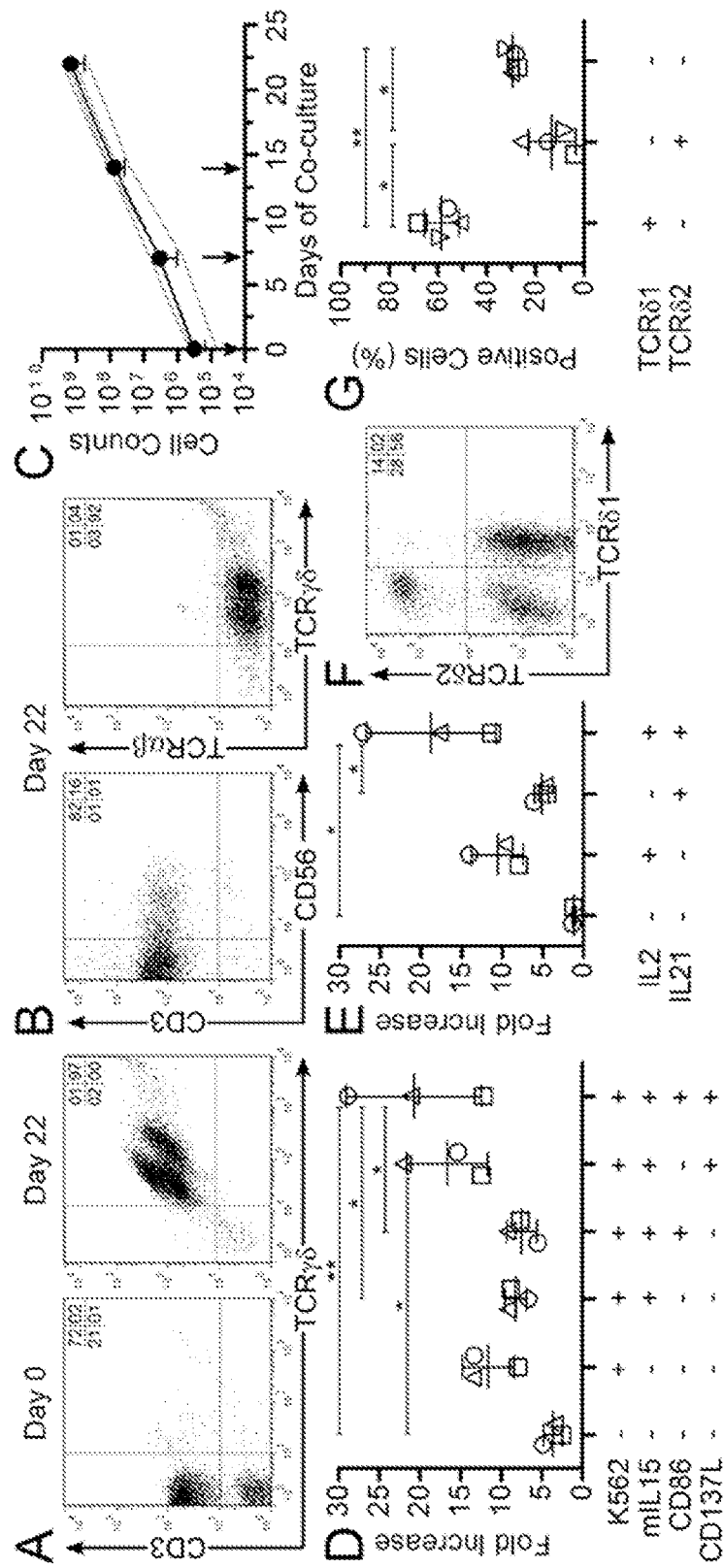
FIGS. 1A-G. Sustained proliferation of PB-derived γδ T cells on γ-irradiated aAPC in presence of IL-2 and IL-21 as bulk (polyclonal) populations. (A) Frequency of γδ T cells before (Day 0) and after (Day 22) co-culture on aAPC and cytokines. One of seven representative donors is shown from four independent experiments. (B) Expression of CD3, CD56, TCRαβ, and TCRγδ at Day 22 of co-culture. One of seven representative donors is shown from 4 independent experiments. (C) Inferred cell count of polyclonal γδ T cells, where the three arrows represent addition of aAPC. Black line is mean±SD (n=4) pooled from two independent experiments and each gray line is an individual donor. (D) Fold increase over nine days of γδ T cells co-cultured with IL-2 and IL-21 along with aAPC expressing membrane-bound IL-15 (mIL15), CD86, and/or CD137L. Data are mean±SD (n=3) pooled from two independent experiments and each shape represents an individual donor. Two-way ANOVA with Bonferroni's post-test was used for statistical analysis. *p<0.05; **p<0.01. (E) Fold increase over 9 days of γδ T cells co-cultured with aAPC (clone #4) in the presence of either soluble recombinant IL-2 and/or IL-21. Data are mean±SD (n=3) pooled from two independent experiments where each shape represents an individual donor. Two-way ANOVA with Bonferroni's post-test was used for statistical analysis. *p<0.05. (F) Representative expression of TCRδ1 and TCRδ2 chains on γδ T cells numerically expanded for 22 days on aAPC clone #4 and cytokines. One of four representative donors from two independent experiments is displayed. (G) Frequency of cell surface expression of TCRδ1$^+$TCRδ2$^{neg}$, TCRδ1$^{neg}$TCRδ2$^+$, and TCRδ1$^{neg}$TCRδ2$^{neg}$ chains on polyclonal γδ T cells propagated for 22 days on aAPC (clone #4) and cytokines. Data are mean±SD (n=4) pooled from two independent experiments and each shape represents an individual donor.

Human γδ T cells have natural anti-tumor immunity, but their utility in the clinic is restricted to one lineage (Vγ9Vδ2) even though other γδ T-cell lineages can recognize and kill tumors. A polyclonal approach to γδ T-cell immunotherapy could target multiple ligands on the tumor surface and maximize therapeutic efficacy. However, a clinically-relevant expansion of polyclonal γδ T cells has yet to be achieved. Recognition of multiple ligands on the tumor surface is mediated by the T cell receptor (TCR) expressed on the γδ T cell surface, which is composed of a heterodimer of δ and γ TCR chains. Moreover, γδ T-cell TCR recognizes antigens outside of major histocompatibility complex (MHC) restriction, which is in contrast to αβ T cells that do recognize their antigens in the context of MHC. Therefore, MHC mis-matched γδ T cells could be given to un-related patients and serve as a universal source of tumor-reactive T cells. As such, γδ T cells generated from one donor may be infused into one or more allogeneic recipients that may or may not share HLA with the donor. This provides an "off-the-shelf" therapy in which γδ T cells can be both pre-prepared and infused on demand.

T cells expressing T-cell receptors (TCRs) composed of heterodimers of γ and δ chains exhibit an ability to kill malignant cells, but direct use of cells expressing Vδ1 and Vδ3 isotypes or employing a polyclonal repertoire has yet to be achieved. The inventors engineered artificial antigen presenting cells (aAPC) from the K562 tumor cell line to expand human T cells expressing defined γδ TCRs to clinically-appealing numbers. Propagated γδ T cells were polyclonal as they expressed Vδ1, Vδ2, Vδ3, Vδ5, Vδ7, and Vδ8 with Vγ2, Vγ3, Vγ7, Vγ8, Vγ9, Vγ10, and Vγ11 TCR chains. Populations of naïve, central memory, and effector memory T cells were dominated by expression of Vδ1, Vδ1$^{neg}$Vδ2$^{neg}$, and Vδ2 TCR chains, respectively. Efficiency of T cells to lyse tumor cells followed the order of differentiation (Vδ2>Vδ1$^{neg}$Vδ2$^{neg}$>Vδ1). Ovarian cancer xenografts were significantly eliminated by Vδ subsets and polyclonal γδ T cells, which significantly increased overall survival of treated mice.

The methods provided herein (i) produce polyclonal γδ T cells, (ii) provide for the expansion of the Vδ1 subset in a manner vastly superior to other techniques in both frequency and cell viability, (iii) produce Vδ2 cells with superior viability compared to methods using aminobisphosphonates, which have a toxic component, and (iv) successfully propagate the Vδ1$^{neg}$Vδ2$^{neg}$ subset. The aAPC used in the methods are immediately available for clinical use, therefore, streamlining the clinical translation of this technology. Vδ1 cells have never been directly infused into a human. The Vδ1$^{neg}$Vδ2$^{neg}$ subset has anti-tumor immunity that can now be tested for the first time in humans.

The presently disclosed aAPC expansion technology can propagate seemingly unlimited numbers of polyclonal γδ T cells from limiting starting quantities, obviating current hurdles of (i) limiting starting quantities of circulating γδ T cells, (ii) polarization of initial populations of γδ T cells towards a fixed clonotype, and (iii) the inability of expansion protocols used for other T cells types, i.e., αβ T cells, to sustain γδ T cell proliferation. The presently disclosed technology has the competitive advantages of (i) using aAPC that are currently in a clinical GMP facility, (ii) the ability of aAPC to numerically expand polyclonal γδ T cells to clinically-relevant numbers (>10$^9$ cells) from starting quantities present in small volumes of peripheral blood, and (iii) the use of more than one lineage of γδ T cells with the potential to target multiple molecules of the tumor cell surface to simultaneously minimize the chance for tumor escape from therapy and maximize therapeutic efficacy. These polyclonal γδ T cells were able to kill every tumor type tested (ALL, CML, colon cancer, ovarian cancer, pancreatic cancer), but did not react to normal tissues (B cells) from unrelated individuals. Thus, a large bank of polyclonal γδ T cells with a fixed or desired repertoire could be manufactured and given to unrelated patients safely for the treatment of, for example, cancer.

The present invention results in cell therapy products for adoptive T cell therapies and has at least four potential uses. First, polyclonal γδ T cells can be used as a universal source of tumor reactive T cells that can be given to unrelated individuals. This has commercialization appeal as a universal source of T cells could decrease the costs associated with generating autologous T cells for each patient to be treated. Second, polyclonal γδ T cells can be further manipulated to increase their tumor reactivity, e.g., through introduction of a chimeric antigen receptor (CAR) that targets a specific tumor antigen. Third, polyclonal γδ T cells also have antiviral activity (cytomegalovirus (CMV), Epstein-Barr virus (EBV), and human immunodeficiency virus (HIV)) and can be used as direct immunotherapies for viral infection and/or protection of opportunistic infections in immunocompromised patients, e.g., cancer patients receiving hematopoietic stem cell transplant (HSCT). Fourth, transplant of a universal set of polyclonal γδ T cells may be used in the control of bacterial infection and sepsis.

I. IMMUNE SYSTEM AND IMMUNOTHERAPY

In some embodiments, a medical disorder is treated by transfer of a polyclonal γδ T-cell population that elicits an immune response. In certain embodiments of the present invention, cancer or infection is treated by transfer of a polyclonal γδ T-cell population that elicits an immune response. Thus, a basic understanding of the immunologic responses is necessary.

The cells of the adaptive immune system are a type of leukocyte, called a lymphocyte. B cells and T cells are the major types of lymphocytes. B cells and T cells are derived from the same pluripotent hematopoietic stem cells, and are indistinguishable from one another until after they are activated. B cells play a large role in the humoral immune response, whereas T cells are intimately involved in cell-mediated immune responses. They can be distinguished from other lymphocyte types, such as B cells and NK cells by the presence of a special receptor on their cell surface called the T-cell receptor (TCR). In nearly all other vertebrates, B cells and T cells are produced by stem cells in the bone marrow. T cells travel to and develop in the thymus, from which they derive their name. In humans, approximately 1%-2% of the lymphocyte pool recirculates each hour to optimize the opportunities for antigen-specific lymphocytes to find their specific antigen within the secondary lymphoid tissues.

T lymphocytes arise from hematopoietic stem cells in the bone marrow, and typically migrate to the thymus gland to mature. αβ T cells express a unique antigen binding receptor on their membrane (T-cell receptor), which can only recognize antigen in association with major histocompatibility complex (MHC) molecules on the surface of other cells. γδ T cells are a small subset of circulating T lymphocytes that are distinct from αβ T cells. γδ T cells are able to recognize both peptide and non-peptide antigens that may be derived from either foreign microorganisms or endogenous cellular products induced by stress, such as viral infection or cancer. Unlike αβ T cells, γδ T cells are not MHC-restricted.

Since γδ T cells lack the fine specificity characteristics of αβ T cells, it has been proposed that they represent a more primitive immune mechanism that provides a first-line surveillance function against infection and tumors (Boismenu et al., 1997). Several studies have documented the response of γδ T cells to various viruses, bacteria, and parasites (Bukowski et al., 1994; Wallace et al., 1995; Lang et al., 1995; Elloso et al., 1996) as well as their ability to mediate lysis of tumor cells of various origins (Zocchi et al., 1990; Kitayama et al., 1993; Choudhary et al., 1995). These results suggest that γδ T cells may have therapeutic potential in the treatment of cancer and infectious diseases.

II. METHOD AND COMPOSITIONS RELATED TO THE EMBODIMENTS

In certain aspects, the invention includes a method of making and/or expanding polyclonal γδ T cells that comprises culturing the cells with artificial antigen presenting cells. In certain aspects, the γδ T cells are primary human γδ T cells, such as γδ T cells derived from human peripheral blood mononuclear cells (PBMC), PBMC collected after stimulation with G-CSF, bone marrow, or umbilical cord blood. The cells may be propagated for days, weeks, or months ex vivo as a bulk population in co-culture with aAPCs. Co-cultures may be initiated with 10$^3$, 10$^4$, 10$^5$, 10$^6$, 10$^7$, or 10$^8$ γδ T cells, or any number derivable therein, and 10$^3$, 10$^4$, 10$^5$, 10$^6$, 10$^7$, 10$^8$, or 10$^9$ aAPC, or any number derivable therein. It is preferable that the co-cultures be initiated with a ratio of γδ T cells to aAPC of 1 to 2.

The γδ T cells may be expanded by stimulation with IL-2, or other cytokines that bind the common gamma-chain (e.g., IL-7, IL-12, IL-15, IL-21, and others). The expansion of γδ T cells may be stimulated with 10, 20, 30, 40, 50, 60, 70, 80, 90, or 100 U/mL of IL-2; preferably the expansion is stimulated with 50 U/mL of IL-2. The expansion of γδ T cells may be stimulated with 10, 20, 30, 40, 50, 60, 70, 80, 90, or 100 ng/mL of IL-21; preferably the expansion is stimulated with 30 ng/mL of IL-21. Said stimulations may occur 1, 2, 3, 4, 5, 6, or 7 times per week, preferably 3 times per week. In a further aspect, the expanded γδ T cells may be cryopreserved.

In certain embodiments of the invention, the γδ T cells are delivered to an individual in need thereof, such as an individual may have cancer or an infection. The cells then enhance the individual's immune system to attack the respective cancer, pathogenic cells, or pathogen-infected cells. In some cases, the individual is provided with one or more doses of the γδ T cells. In cases where the individual is provided with two or more doses of the γδ T cells, the duration between the administrations should be sufficient to allow time for propagation in the individual, and in specific embodiments the duration between doses is 1, 2, 3, 4, 5, 6, 7, or more days. The γδ T cells may be allogeneic or autologous to the patient.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In some aspects, the γδ T cells are obtained from a bank of umbilical cord blood, peripheral blood, human embryonic stem cells, or induced pluripotent stem cells, for example. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the present invention can be used alone or in combination with other well-established agents useful for treating cancer or infectious diseases. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. Local or systemic delivery can be accomplished by administration comprising application or instillation of the formulation into body cavities or by parenteral introduction comprising intramuscular, intravenous, intraportal, intrahepatic, peritoneal, subcutaneous, or intradermal administration.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated, polyclonal γδ T cells is present in the composition and introduced into the subject such that long-term, specific, anti-tumor responses are established to reduce the size of a tumor or eliminate tumor growth or regrowth than would otherwise result in the absence of such treatment. Desirably, the amount of polyclonal γδ T cells introduced into the subject causes a 10%, 20%, 30%, 40%, 50%, 60%, 70%, 80%, 90%, 95%, 98%, or 100% decrease in tumor size when compared to otherwise same conditions wherein the polyclonal γδ T cells are not present.

Accordingly, the amount of polyclonal γδ T cells administered should take into account the route of administration and should be such that a sufficient number of the polyclonal γδ T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of polyclonal γδ T cells desirably should be sufficient to provide in the subject being treated at least from about $1 \times 10^6$ to about $1 \times 10^9$ polyclonal γδ T cells, even more desirably, from about $1 \times 10^7$ to about $5 \times 10^8$ polyclonal γδ T cells, although any suitable amount can be utilized either above, e.g., greater than $5 \times 10^8$ cells, or below, e.g., less than $1 \times 10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of polyclonal γδ T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

III. ARTIFICIAL ANTIGEN PRESENTING CELLS

In some cases, aAPCs are useful in preparing therapeutic compositions and cell therapy products of the embodiments. For general guidance regarding the preparation and use of antigen-presenting systems, see, e.g., U.S. Pat. Nos. 6,225, 042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2 (see, Kim et al., 2004). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

In other preferred embodiments, the aAPCs may be inactivated (e.g., by chemical treatment or irradiation), so that essentially no cell growth or replication occurs after the inactivation. Thus inactivation maintains the important APC functions of aAPCs while helping to alleviate concerns about safety of a cell therapy product developed using the aAPCs. For methods related to crosslinking and aAPCs, see for example, U.S. Patent Application Publication No. 2009/0017000, which is incorporated herein by reference. Subsequently, an inactivated aAPC culture may be maintained for as long a time as is appropriate to activate and enrich for a therapeutically effective population of polyclonal γδ T cells.

IV. CHIMERIC ANTIGEN RECEPTORS

The term "chimeric antigen receptors (CARs)," as used herein, may refer to artificial T-cell receptors T-bodies, single-chain immunoreceptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain that may vary in length and comprises a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "T-cell receptor (TCR)" as used herein refers to a protein receptor on T cells that is composed of a heterodimer of a gamma and a delta (γ/δ) chain. In embodiments of the invention, the TCR may be modified on any cell comprising a TCR, including a helper T cell, a cytotoxic T cell, a memory T cell, regulatory T cell, natural killer T cell, and gamma delta T cell, for example.

As used herein, the term "antigen" is a molecule capable of being bound by an antibody or T-cell receptor. An antigen is additionally capable of inducing a humoral immune response and/or cellular immune response leading to the production of B and/or T lymphocytes.

Embodiments of the present invention involve nucleic acids, including nucleic acids encoding an antigen-specific chimeric antigen receptor (CAR) polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprised of the shared space between one or more antigens. Pattern recognition receptors, such as Dectin-1, may be used to derive specificity to a carbohydrate antigen. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR αβ chain) regions.

It is contemplated that the human CAR nucleic acids are human genes to enhance cellular immunotherapy for human patients. In a specific embodiment, the invention includes a full length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into what has been referred to as a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

The intracellular signaling domain of the chimeric receptor of the invention is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Effector function in a naive, stem-cell like, memory, or memory-type T cell includes antigen-dependent proliferation. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal. Examples include the zeta chain of the T-cell receptor or any of its homologs (e.g., eta, delta, gamma, or epsilon), MB1 chain, B29, Fc RIII, Fc RI, and combinations of signaling molecules, such as CD3 and CD28, CD27, 4-1BB, DAP-10, OX40, and combinations thereof, as well as other similar molecules and fragments as well as mutations to the signaling moieties such as modifying the ITAMs. Intracellular signaling portions of other members of the families of activating proteins can be used, such as FcγRIII and FcεRI.

The antigen-specific extracellular domain and the intracellular signaling-domain may be linked by a transmembrane domain, such as the human IgG$_4$Fc hinge and Fc regions. Alternatives include the human CD4 transmembrane domain, the human CD28 transmembrane domain, the transmembrane human CD3ζ domain, or one or more cysteine-mutated human CD3ζ domain(s), or other transmembrane domains from other human transmembrane signaling proteins, such as CD16 and CD8 and erythropoietin receptor.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3ζ, an additional signal provided by a human costimulatory receptor inserted in a human CAR is important for full activation of T cells and could help improve in vivo persistence and the therapeutic success of the adoptive immunotherapy.

In particular embodiments, the invention concerns isolated nucleic acid segments and expression cassettes incorporating DNA sequences that encode the CAR. Vectors of the present invention are designed, primarily, to deliver desired genes to immune cells, preferably T cells under the control of regulated eukaryotic promoters, for example, MNDU3 promoter, CMV promoter, EF1 alpha promoter, or Ubiquitin promoter. Also, the vectors may contain a selectable marker, if for no other reason, to facilitate their manipulation in vitro. In other embodiments, the CAR can be expressed from mRNA in vitro transcribed from a DNA template.

Chimeric antigen receptor molecules are recombinant and are distinguished by their ability to both bind antigen and transduce activation signals via one or more immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they bind native antigen on the target cell surface in an HLA-independent fashion. For example, several laboratories have reported on scFv constructs fused to sequences coding for the intracellular portion of the CD3 complex's zeta chain (ζ) the Fc receptor gamma chain, and sky tyrosine kinase. Re-directed T cell effector mechanisms including tumor recognition and lysis by CTL have been documented in several murine and human antigen-scFv: ζ systems.

To date non-human antigen binding regions are typically used in constructing a chimeric antigen receptor. A potential problem with using non-human antigen binding regions, such as murine monoclonal antibodies, is the lack of human effector functionality and inability to penetrate into tumor masses. In other words, such antibodies may be unable to mediate complement-dependent lysis or lyse human target cells through antibody-dependent cellular toxicity or Fc-receptor mediated phagocytosis to destroy cells expressing CAR. Furthermore, non-human monoclonal antibodies can be recognized by the human host as a foreign protein, and therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response. Therefore, the use of human antibodies is more preferred because they do not elicit as strong a HAMA response as murine antibodies. Similarly, the use of human sequences in the CAR can avoid immune-mediated recognition and therefore elimination by endogenous T cells that reside in the recipient and recognize processed antigen in the context of HLA.

In some embodiments, the chimeric antigen receptor comprises: a) an intracellular signaling domain, b) a transmembrane domain, and c) an extracellular domain comprising an antigen binding region.

In specific embodiments, intracellular receptor signaling domains in the CAR include those of the T cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example.

In certain embodiments of the chimeric antigen receptor, the antigen-specific portion of the receptor (which may be referred to as an extracellular domain comprising an antigen binding region) comprises a tumor associated antigen or a pathogen-specific antigen binding domain including carbohydrate antigen recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, tyrosine-protein kinase transmembrane receptor (ROR)1, CA-125, MUC-1, CD56, EGFR, c-Met, AKT, Her2, Her3, epithelial tumor antigen, melanoma-associated antigen, mutated p53, mutated ras, and so forth. In certain embodiments, the CAR can be co-expressed with a membrane-bound cytokine to improve persistence when there is a low amount of tumor-associated antigen. For example, CAR can be co-expressed with membrane-bound IL-15.

In certain embodiments intracellular tumor associated antigens may be targeted, such as HA-1, survivin, WT1, and p53. This can be achieved by a CAR expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA.

The pathogen may be of any kind, but in specific embodiments the pathogen is a fungus, bacteria, or virus, for example. Exemplary viral pathogens include those of the families of Adenoviridae, EpsteinBarr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes*, and *Salmonella*. In one embodiment the pathogen receptor Dectin-1 can be used to generate a CAR that recognizes the carbohydrate structure on the cell wall of fungi. T cells genetically modified to express the CAR based on the specificity of Dectin-1 can recognize *Aspergillus* and target hyphal growth. In another embodiment, CARs can be made based on an antibody recognizing viral determinants (e.g., the glycoproteins from CMV and Ebola) to interrupt viral infections and pathology.

In some embodiments, the pathogenic antigen is an *Aspergillus* carbohydrate antigen for which the extracellular domain in the CAR recognizes patterns of carbohydrates of the fungal cell wall, such as via Dectin-1.

A chimeric immunoreceptor according to the present invention can be produced by any means known in the art, though preferably it is produced using recombinant DNA techniques. A nucleic acid sequence encoding the several regions of the chimeric receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic T-cell line.

As used herein, a nucleic acid construct or nucleic acid sequence or polynucleotide is intended to mean a DNA molecule that can be transformed or introduced into a T cell and be transcribed and translated to produce a product (e.g., a chimeric antigen receptor).

In an exemplary nucleic acid construct (polynucleotide) employed in the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., a CD4 promoter). The promoter can be constitutive or inducible, where induction is associated with the specific cell type or a specific level of maturation, for example. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression. Also, it may be further advantageous to use endogenous or exogenous non-coding regions to stabilize the mRNA.

For expression of a chimeric antigen receptor of the present invention, the naturally occurring or endogenous transcriptional initiation region of the nucleic acid sequence encoding N-terminal components of the chimeric receptor can be used to generate the chimeric receptor in the target host. Alternatively, an exogenous transcriptional initiation region can be used that allows for constitutive or inducible expression, wherein expression can be controlled depending upon the target host, the level of expression desired, the nature of the target host, and the like.

Likewise, a signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region may be provided by the naturally occurring or endogenous transcriptional termination region of the nucleic acid sequence encoding the C-terminal component of the chimeric receptor. Alternatively, the termination region may be derived from a different source. For the most part, the source of the termination region is generally not considered to be critical to the expression of a recombinant protein and a wide variety of termination regions can be employed without adversely affecting expression.

As will be appreciated by one of skill in the art that, in some instances, a few amino acids at the ends of the antigen binding domain in the CAR can be deleted, usually not more than 10, more usually not more than 5 residues, for example. Also, it may be desirable to introduce a small number of amino acids at the borders, usually not more than 10, more usually not more than 5 residues. The deletion or insertion of amino acids may be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct that encodes the chimeric receptor according to the invention can be prepared in conventional ways. Because, for the most part, natural sequences may be employed, the natural genes may be isolated and manipulated, as appropriate, so as to allow for the proper joining of the various components. Thus, the nucleic acid sequences encoding for the N-terminal and C-terminal proteins of the chimeric receptor can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired chimeric receptor. The sequence can be screened by restriction analysis, sequencing, or the like.

The chimeric constructs of the present invention find application in subjects having or suspected of having cancer by reducing the size of a tumor or preventing the growth or re-growth of a tumor in these subjects. Accordingly, the present invention further relates to a method for reducing growth or preventing tumor formation in a subject by introducing a chimeric construct of the present invention into an isolated T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISO-CELL™ from Pierce, Rockford, Ill.).

It is contemplated that the chimeric construct can be introduced into the subject's own T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Alternatively, non-viral vectors can be used, such as DNA and mRNA species that participate in transportation, which includes the Sleeping Beauty system. Other plasmids include DNA species that exist as episomal plasmids. Suitable vectors for use in accordance with the method of the present invention are non-replicating in the subject's T cells. A large number of vectors are known that are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV, HSV, or BPV.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject. To facilitate administration, the transduced T cells according to the invention can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric receptor. Thus, desirably the transduced T cells can be made into a pharmaceutical composition containing a balanced salt solution, preferably Hanks' balanced salt solution, or normal saline.

V. KITS OF THE INVENTION

Any of the compositions described herein may be comprised in a kit. In some embodiments, allogeneic, polyclonal γδ T cells are provided in the kit, which also may include reagents suitable for expanding the cells, such as media, aAPCs, growth factors, and/or cytokines.

The kits may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present invention also will typically include a means for containing the polyclonal γδ T cells and any other reagent containers in close confinement for commercial sale. Such containers may include injection or blow molded plastic containers into which the desired vials are retained, for example.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Subsets of γδ T Cells for Cancer Immunotherapy

Given that γδ T cells have endogenous anti-cancer activity, such as against K562 cells (D'Asaro et al., 2010; Lamb et al., 1999), the inventors tested whether tumor cells would serve a cellular substrate to propagate polyclonal γδ T cells. K562 cells have been genetically modified to function as artificial antigen presenting cells (aAPC) to activate and numerically expand αβ T cells and NK cells ex vivo (Denman et al., 2012; Maus et al., 2002; Numbenjapon et al., 2006; Singh et al., 2013; Suhoski et al., 2007). The inventors determined that γ-irradiated K562-derived aAPC (designated clone #4, genetically modified to co-express CD19, CD64, CD86, CD137L, and a membrane-bound mutein of IL-15; mIL15) in combination with cytokines can sustain the proliferation of polyclonal T cells expressing Vδ1, Vδ2, Vδ3, Vδ5, Vδ7, and Vδ8 with Vγ2, Vγ3, Vγ7, Vγ8, Vγ9, Vγ10, and Vγ11 TCRs. The inventors demonstrate that these subsets differ with respect to differentiation status (nave, central memory, and effector memory) and vary in their ability to kill tumor cells. These comparisons have implications for adoptive immunotherapy, cancer biology, and immunology.

Ex Vivo Numeric Expansion of Polyclonal γδ T Cells on aAPC Depends on Co-Stimulation and Cytokines.

The adoptive transfer of γδ T cells requires ex vivo propagation since starting numbers from peripheral blood mononuclear cells (PBMC) are limiting (gating on lymphocyte pool: 3.2%±1.2%; mean±standard deviation (SD); n=4). The γδ T cells isolated from PBMC were co-cultured for 22 days on γ-irradiated K562-derived aAPC (clone #4)

engineered to express co-stimulatory molecules in the presence of soluble recombinant IL-2 and IL-21, which resulted in the outgrowth of a population of T cells homogeneously co-expressing CD3 and TCR γδ (97.9%±0.6%; mean±SD; n=4; FIG. 1A). NK cells (CD3$^{neg}$CD56$^+$) and αβ T cells (TCR aft) were absent from these cultures (FIG. 1B). This approach to propagation yielded >10$^9$ γδ T cells from <10$^6$ total initiating cells in three weeks (FIG. 1C), which represented a 4.9×10$^3$±1.7×10$^3$ (mean±SD; n=4) fold increase. Populations of TCRδ1$^+$TCRδ2$^{neg}$, TCRδ1$^{neg}$TCRδ2$^+$, and TCRδ1$^{neg}$TCRδ2$^{neg}$ were detected following co-culture indicating that aAPC supported polyclonal γδ T cell proliferation (FIGS. 1F and 1G). Thus, aAPC and recombinant human cytokines supported the robust numeric expansion of polyclonal γδ T cells from small starting numbers of γδ T cells derived from PBMC.

The addition of exogenous cytokines and presence of co-stimulatory molecules (mIL15, CD86, and CD137L) on aAPC were assessed for their ability to support the outgrowth of γδ T cells. Parental K562 cells were genetically modified to express individual co-stimulatory molecules and cloned to achieve homogeneous expression (FIG. 2) to assess the impact of introduced molecules on proliferation of γδ T cells. Co-cultures with exogenous IL-2 and IL-21 were initiated with γδ T cells and five sets of γ-irradiated K562: (i) parental, (ii) mIL15$^+$, (iii) mIL15$^+$CD86$^+$, (iv) mIL15$^+$CD137L$^+$, and (v) mIL15$^+$CD86$^+$CD137L$^+$ (clone #4). γδ T cells were cultured in parallel with cytokines and no APC demonstrating that soluble IL-2 and IL-21 supported only limited numeric expansion of γδ T cells (FIG. 1D). Propagation increased when parental K562 cells were added, indicating that endogenous molecules on these cells can activate γδ T cells for proliferation. The expression of mIL15 with or without CD86 did not appear to further improve the ability of γδ T cells to propagate compared with parental K562. In contrast, significantly higher rates of propagation of γδ T cells was observed with co-culture of mIL15$^+$CD137L$^+$ and mIL15$^+$CD86$^+$CD137L$^+$aAPC. Thus, it appears that CD137L is important to sustain the proliferation of γδ T cells on K562 cells in the presence of cytokines. When IL-2 and IL-21 were removed from the co-culture on clone #4, the proliferation of γδ T cells ceased, and together these cytokines exhibited an additive benefit to the rate of γδ T cell propagation (FIG. 1E). This validated the approach to combining aAPC clone #4 with both IL-2 and IL-21 to drive the proliferation of γδ T cells ex vivo.

Ex Vivo Numeric Expansion of Neonatal γδ T Cells on aAPC.

Figure 3:
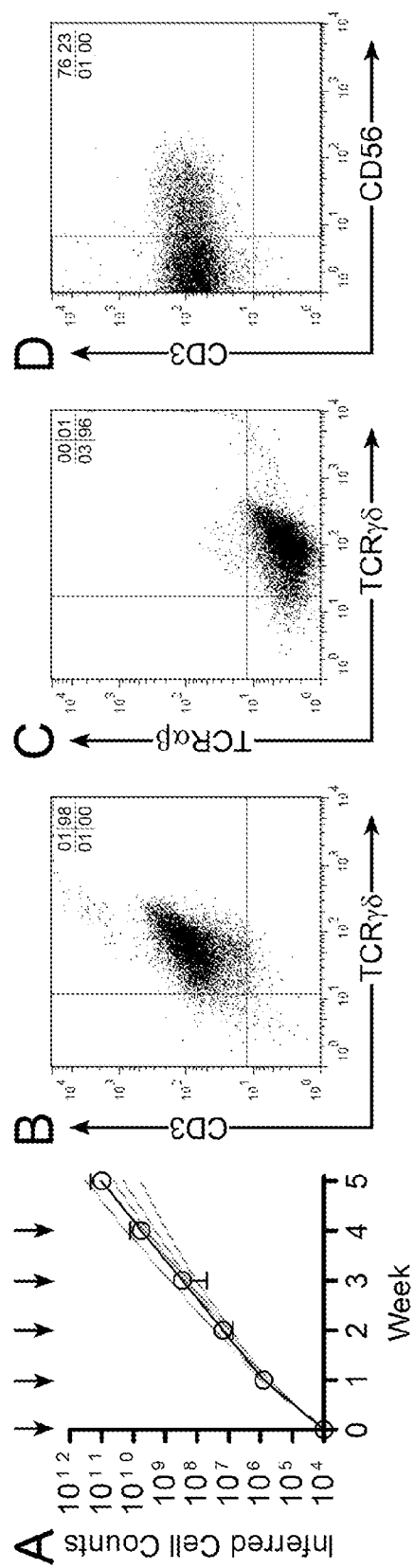
FIGS. 3A-D. Expansion of UCB-derived γδ T cells on aAPC. γδ T cells were sorted by FACS based on staining with CD3 and TCRγδ and stimulated weekly with aAPC clone #4 in presence of soluble recombinant IL-2 and IL-21. (A) Total inferred cell numbers from co-cultures where black line represents the mean±SD (n=5) pooled from four independent experiments and gray lines are individual donors. Arrows represent the addition of γ-irradiated aAPC. Expression of (B) CD3 (y-axis) and TCRγδ (x-axis), (C) TCRαβ (y-axis) and TCRγδ (x-axis), and (D) CD3 (y-axis) and CD56 (x-axis) of a representative donor (1 of 5 from four independent experiments) by flow cytometry after five weeks of expansion on aAPC with IL-2 and IL-21. Quadrant frequencies are displayed in upper right corners.

Allogeneic umbilical cord blood (UCB) is used to restore hematopoiesis in patients undergoing hematopoietic stem-cell transplantation (HSCT). The limited abundance of mononuclear cells within an UCB unit collected to restore hematopoiesis curtails the number of neonatal γδ T cells directly available for adoptive transfer. Thus, the inventors evaluated whether aAPC would sustain proliferation from reduced starting numbers of γδ T cells. Fluorescence activated cell sorting (FACS) was used to isolate 10$^4$ UCB-derived γδ T cells (~0.01% of a typical UCB unit) which were co-cultured on aAPC clone #4 with IL-2 and IL-21. After 35 days, there was a 10$^7$-fold increase in cell number, as an average of 10$^{11}$ UCB-derived γδ T cells (Range: 6×10$^9$-3×10$^{11}$; n=5) were propagated from the 10$^4$ initiating γδ T cells (FIG. 3A). Two additional stimulations were performed for γδ T cells derived from UCB compared to PBMC to highlight their potential for proliferating to clinically-relevant numbers. The γδ T-cell populations exhibited uniform co-expression of CD3 and TCRγδ (FIG. 3B) and lacked TCRαβ$^+$ T cells (FIG. 3C) and CD3$^{neg}$CD56$^+$ NK cells (FIG. 3D). Collectively, these data demonstrate that aAPC clone #4 when used with IL-2 and IL-21 could sustain the ex vivo proliferation of UCB-derived γδ T cells from small starting populations.

γδ T Cells Express Polyclonal and Defined TCRγδ Repertoire Following Propagation on aAPC.

Figure 4:
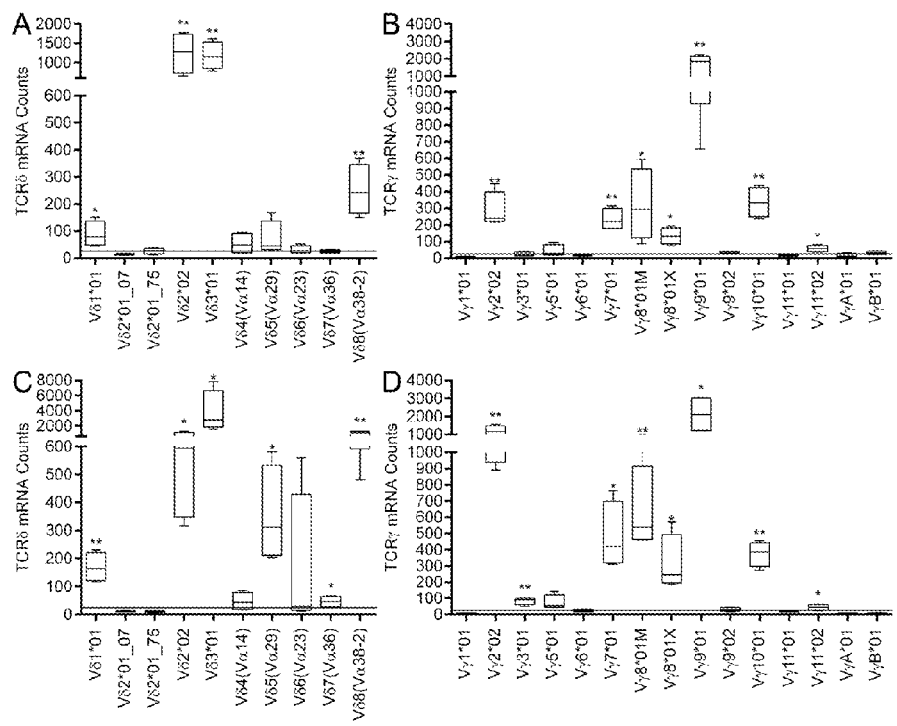
FIGS. 4A-D. Abundance of Vδ and Vγ mRNA in γδ T cells propagated and activated on aAPC. Quantification of mRNA species coding for (A) Vδ and (B) Vγ alleles in PBMC-derived γδ T cells by DTEA at day 22 of co-culture on aAPC/IL-2/IL-21. Quantification of mRNA species coding for (C) Vδ and (D) Vγ alleles in UCB-derived γδ T cells by DTEA at day 34-35 of co-culture on aAPC/IL-2/IL-21 as described for PBMC. Box-and-whiskers plots display 25% and 75% percentiles where lines represent maximum, mean, and minimum from top to bottom (n=4). Solid lines at bottom of graphs represent limit-of-detection (LOD) calculated from mean±2×SD of DTEA negative controls. Student's paired 1-tailed t-tests were performed for each allele relative to the sample LOD. *p<0.05 and **p<0.01

Upon establishing that γδ T cells could numerically expand on aAPC, the inventors sought to determine the TCR repertoire of the propagated cells. A non-enzymatic digital multiplex array termed "direct TCR expression array" (DTEA) that quantifies the diversity of TCR expression in γδ T cells was employed here to assess if aAPC-expanded γδ T cells exhibited a polyclonal TCR repertoire (Zhang et al., 2012). Four of eight Vδ alleles (Vδ1, Vδ2, Vδ3, and Vδ8) (FIG. 4A) were detected in PBMC-derived γδ T cells and were co-expressed with Vγ2, Vγ7, Vγ8 (two alleles), Vγ9, Vγ10, and Vγ 11 (FIG. 4B). Similarly, polyclonal TCR repertoire of Vδ and Vγ chains was observed in γδ T cells expanded from UCB (FIGS. 4C and 4D) albeit with reduced abundance of Vδ2 cells, more Vγ2 and presence of Vγ3, Vδ5, and Vδ7 cells not seen from PBMC. Thus, aAPC expanded γδ T cells maintaining a polyclonal TCR repertoire from both PBMC and UCB.

Figure 5:
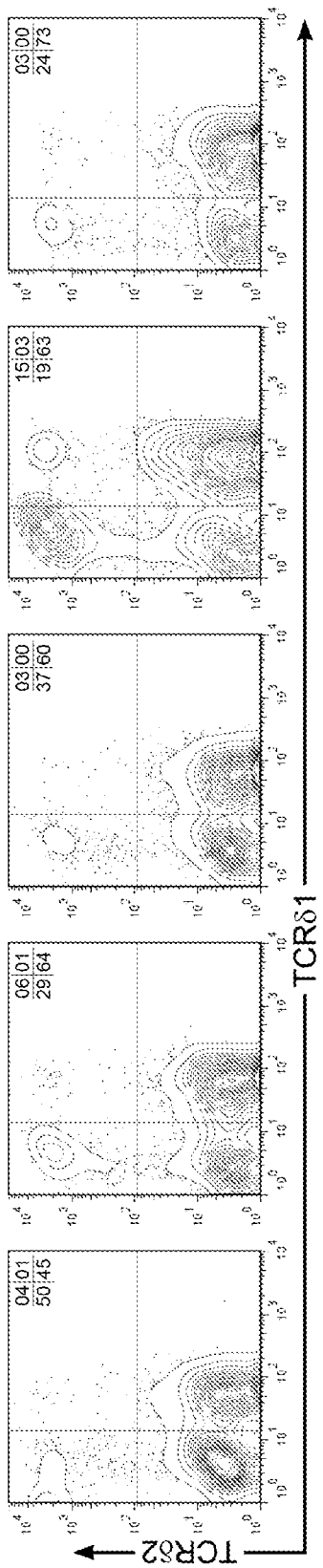
FIG. 5. Surface expression of TCRδ1 and TCRδ2 chains on γδ T cells derived from UCB and propagated on aAPC. Expression by flow cytometry of TCRδ2 (y-axes) and TCRδ1 (x-axes) on γδ T cells derived from UCB following 35 days of co-culture on aAPC clone #4 in presence of IL-2 and IL-21. Quadrant frequencies (percentage) are displayed in upper right corners. T cells were propagated in four independent experiments.
Figure 6:
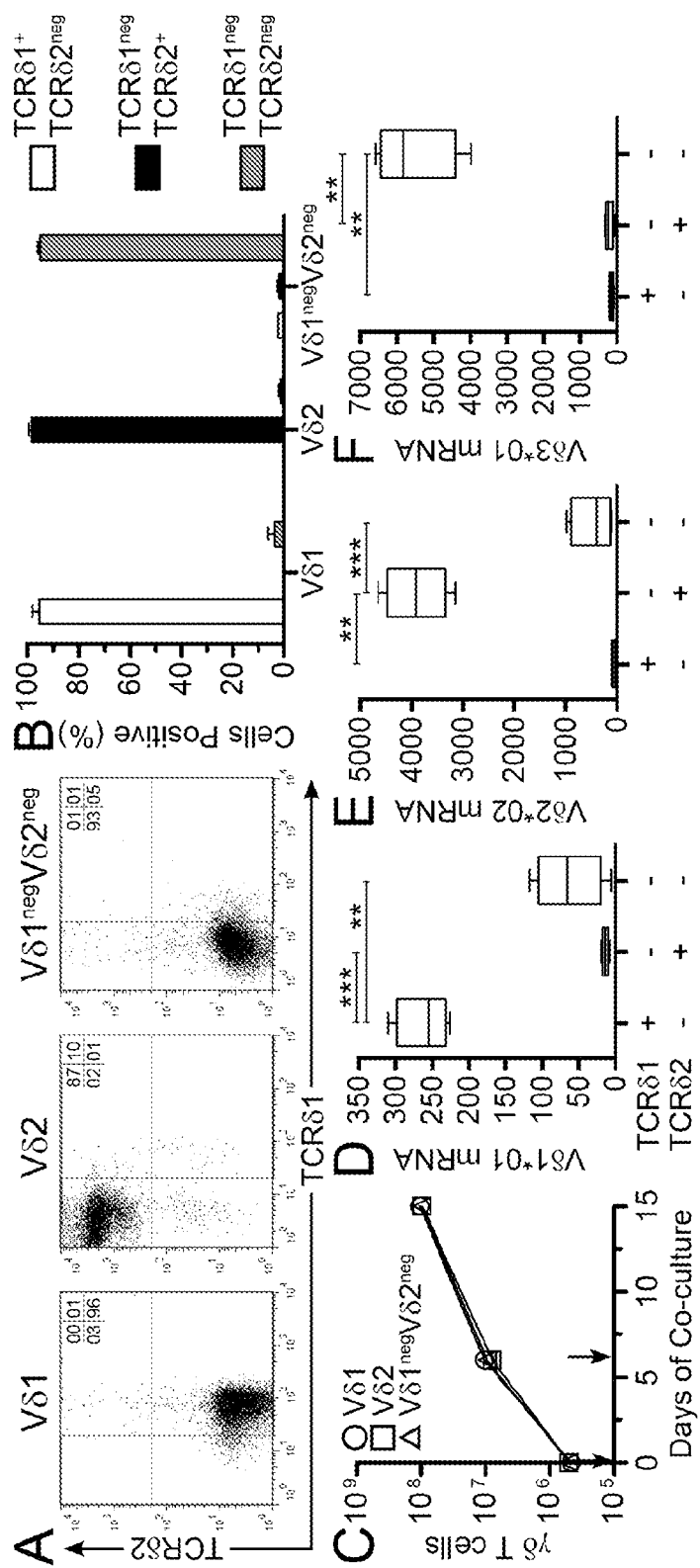
FIGS. 6A-F. Sustained proliferation of PB-derived Vδ T cell subsets as separated populations on γ-irradiated aAPC in presence of IL-2 and IL-21. After two 7-day stimulations with aAPC (clone #4) and cytokines the bulk population of γδ T cells were separated into Vδ1, Vδ2, and Vδ1$^{neg}$Vδ2$^{neg}$ subsets by FACS based on staining of T cells defined as TCRδ1$^+$TCRδ2$^{neg}$, TCRδ1$^{neg}$TCRδ2$^+$, and TCRδ1$^{neg}$TCRδ2$^{neg}$, respectively. (A) Expression of TCRδ1 and TCRδ2 chains on Vδ1, Vδ2, and Vδ1$^{neg}$Vδ2$^{neg}$ subsets of γδ T cells (from left to right) after 15 days of numeric expansion on aAPC and cytokines as isolated groups. One of four representative donors is shown pooled from two independent experiments. Quadrant frequencies (percentage) within flow plots are displayed in upper right corners. (B) Frequency of TCRδ1$^+$TCRδ2$^{neg}$ (open bars), TCRδ1$^{neg}$TCRδ2$^+$ (black bars), and TCRδ1$^{neg}$TCRδ2$^{neg}$ (gray bars) cell surface protein expression in subsets of γδ T cells after 15 days numeric expansion on aAPC and cytokines as isolated groups. Data are mean±SD (n=4) pooled from two independent experiments. (C) Proliferation of each isolated Vδ subset stimulated twice with aAPC clone #4 (arrows) in presence of cytokines and total cell counts are displayed. Data are mean±SD (n=4) pooled from two independent experiments. (D-F) Direct TCR expression array (DTEA) was used to identify and measure abundance of mRNA species coding for (D) Vδ1*01, (E) Vδ2*02, and (F) Vδ3*01 in γδ T-cell sub-populations after 15 days of proliferation on aAPC and cytokines as separated subsets. Box-and-whiskers plots display 25% and 75% percentiles where lines represent maximum, mean, and minimum from top to bottom (n=4). Student's paired, 2-tailed t-tests were done for statistical analyses. p<0.01 and *p<0.001
Figure 7:
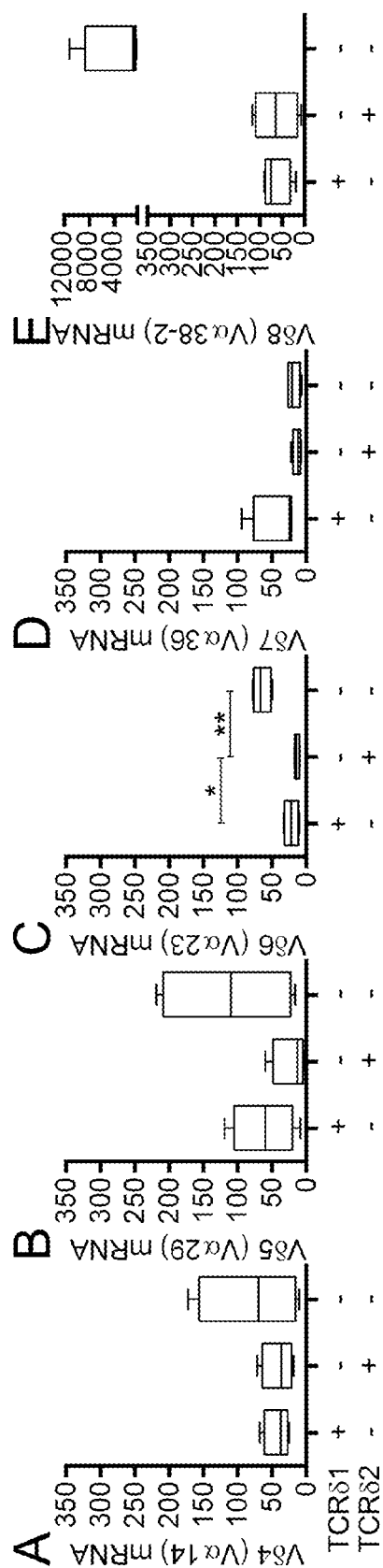
FIGS. 7A-E. mRNA expression of shared Vα/Vδ alleles in γδ T cells separated and expanded on aAPC, IL-2, and IL-21. Expression of shared Vδ and Vα alleles by DTEA following 15 days of co-culture of Vδ1, Vδ2, and Vδ1$^{neg}$Vδ2$^{neg}$ populations on aAPC clone #4 in presence of IL-2 and IL-21. Detection of (A) Vδ4 (Vα14), (B) Vδ5 (Vα29), (C) Vδ6 (Vα23), (D) Vδ7 (Vα36), and (E) Vδ8 (Vα38-2) in each separated subset. Box-and-whiskers plots display 25% and 75% percentiles where lines represent maximum, mean, and minimum from top to bottom (n=4). Student's paired, 2-way t-tests performed for statistical analysis between populations.

The inventors sought to validate these mRNA data by sorting polyclonal populations with TCRδ-specific antibodies and repeating DTEA on isolated cultures. There are only two TCRδ-specific mAbs commercially available and they identified three discrete Vδ populations (Vδ1: TCRδ1$^+$TCRδ2$^{neg}$, Vδ2: TCRδ1$^{neg}$TCRδ2$^+$, and Vδ1$^{neg}$Vδ2$^{neg}$: TCRδ1$^{neg}$TCRδ2$^{neg}$) within aAPC-expanded γδ T cells from PBMC (FIGS. 1F and 1G) and UCB (FIG. 5) with TCRδ frequencies following Vδ1>Vδ1$^{neg}$Vδ2$^{neg}$>Vδ2, which corroborated DTEA. FACS isolated subsets from PBMC-derived γδ T-cell pools were propagated with clone #4 as discrete populations, which maintained their identity as assessed by expression of TCRδ isotypes (FIGS. 6A and 6B) and no differences in rates of proliferation on aAPC were observed between sorted subsets (FIG. 6C). DTEA demonstrated that these isolated Vδ1, Vδ2, and Vδ1$^{neg}$Vδ2$^{neg}$ populations predominantly expressed Vδ1*01 (FIG. 6D), Vδ2*02 (FIG. 6E), and Vδ3*01 (FIG. 6F) mRNA, respectively. Expression of other Vδ2 alleles (Vδ1*01_07 and Vδ1*01_75) was absent from polyclonal γδ T cells (FIG. 4A) and each of the sorted subsets. Small amounts of Vδ4 (FIG. 7A), Vδ5 (FIG. 7B), Vδ6 (FIG. 7C), and Vδ7 (FIG. 7D) mRNA species were detected in the three subsets of T cells sorted for Vδ expression. Vδ8 mRNA was exclusively present in sorted Vδ1$^{neg}$Vδ2$^{neg}$ cells (FIG. 7E) and likely these T cells are the main contributors of Vδ8 in bulk γδ T cells from PBMC (FIG. 4A). Collectively, these results (i) show that isolated Vδ1 and Vδ2 subsets were pure with regards to Vδ mRNA expression, (ii) demonstrate that TCRδ1$^{neg}$TCRδ2$^{neg}$γδ T cells from PBMC primarily expressed Vδ3 and Vδ8 mRNA, and (iii) establish that Vδ1, Vδ2, and Vδ1$^{neg}$Vδ2$^{neg}$ T-cell subsets could be separately propagated on aAPC.

Figure 8:
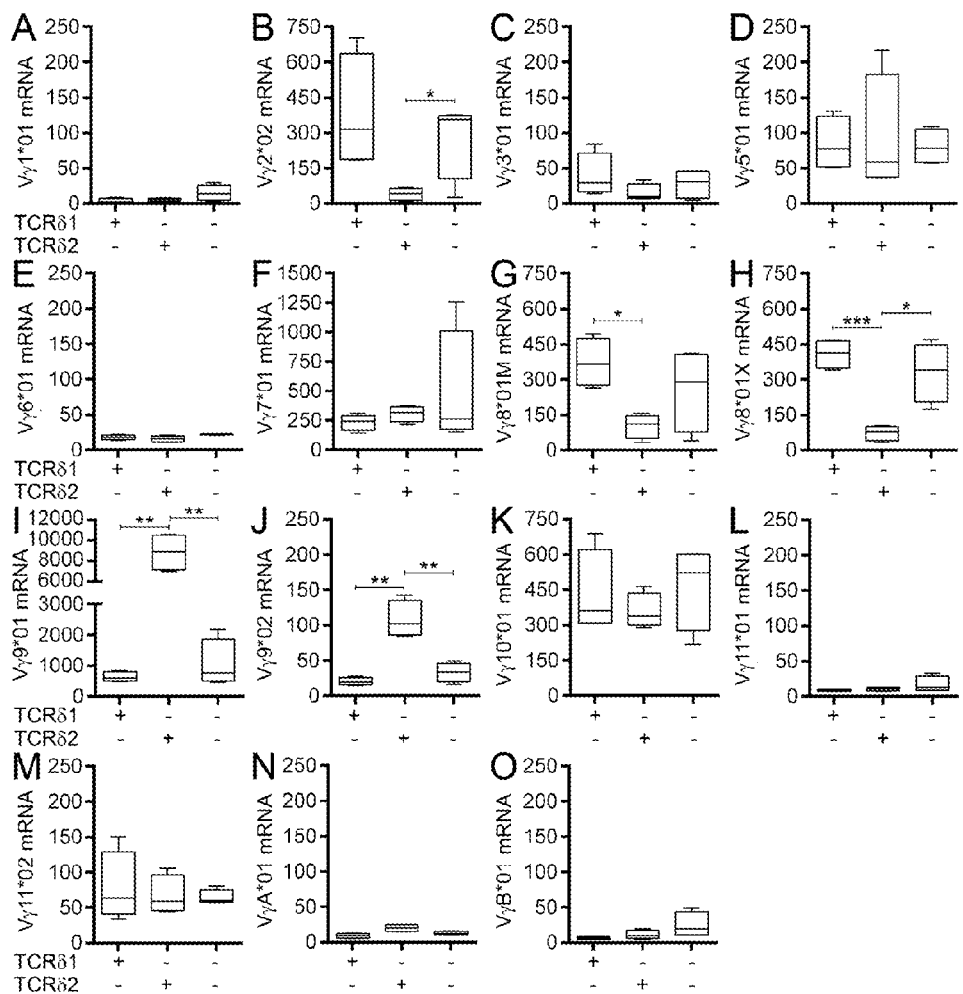
FIGS. 8A-O. Abundance of mRNA species coding for Vγ chains in γδ T-cell subsets. Polyclonal γδ T cells from PB were stimulated twice with aAPC clone #4 in presence of IL-2 and IL-21 and then FACS separated into TCRδ1$^+$TCRδ2$^{neg}$, TCRδ1$^{neg}$TCRδ2$^+$, and TCRδ1$^{neg}$TCRδ2$^{neg}$ subpopulations. These were then stimulated as isolated subsets two more times with aAPC clone #4 in presence of IL-2 and IL-21. DTEA was used to identify and quantify mRNA coding for (A) Vγ1*01, (B) Vγ2*02, (C) Vγ3*01, (D) Vγ5*01, (E) Vγ6*01, (F) Vγ7*01, (G) Vγ8*01M, (H) Vγ8*01X, (I) Vγ9*01, (J) Vγ9*02, (K) Vγ10*01, (L) Vγ11*01, (M) Vγ 11*02, (N) Vγ A*01, and (O) VγB*01. Box-and-whiskers plots display 25% and 75% percentiles where lines represent maximum, mean, and minimum from top to bottom (n=4). Student's paired 2-tailed t-tests were performed for each allele between the Vδ-sorted populations. *p<0.05 and **p<0.01

DTEA was then used to evaluate Vγ TCR usage to gain insight into allelic pairing and Vγ repertoire within each of the three isolated Vδ subsets. Overall, Vδ1 and Vδ1$^{neg}$Vδ2$^{neg}$ subsets were not different in their pairing with Vγ chains (p=0.419; Two-way ANOVA), but Vγ expression was significantly different in Vδ2 T cells compared to both Vδ1 T cells (p<0.0001) and Vδ1$^{neg}$Vδ2$^{neg}$ T cells (p<0.0001). This was also observed in the trends for each Vγ allele where Vδ1 and Vδ1$^{neg}$Vδ2$^{neg}$ T cells were distinct from Vδ2 T cells (FIG. 8). Indeed, significant differences were detected between Vδ subsets regarding abundance of Vγ2*02 (FIG. 8B), Vγ8*01M (FIG. 8G), Vγ *01X (FIG. 8H), Vγ9*01 (FIG. 8I), and Vγ9*02 (FIG. 8J) mRNA species. Thus, the diverse Vγ mRNA usage within each Vδ subset reinforces the polyclonal repertoire achieved upon propagation on aAPC with IL-2 and IL-21. To our knowledge, this is the most detailed assessment of Vγ usage among T cells expressing Vδ1, Vδ2, and Vδ1$^{neg}$Vδ2$^{neg}$ subsets to date.

Propagated γδ T-Cell Subsets Express Distinct Markers Predictive of their Therapeutic Potential.

Figure 9:
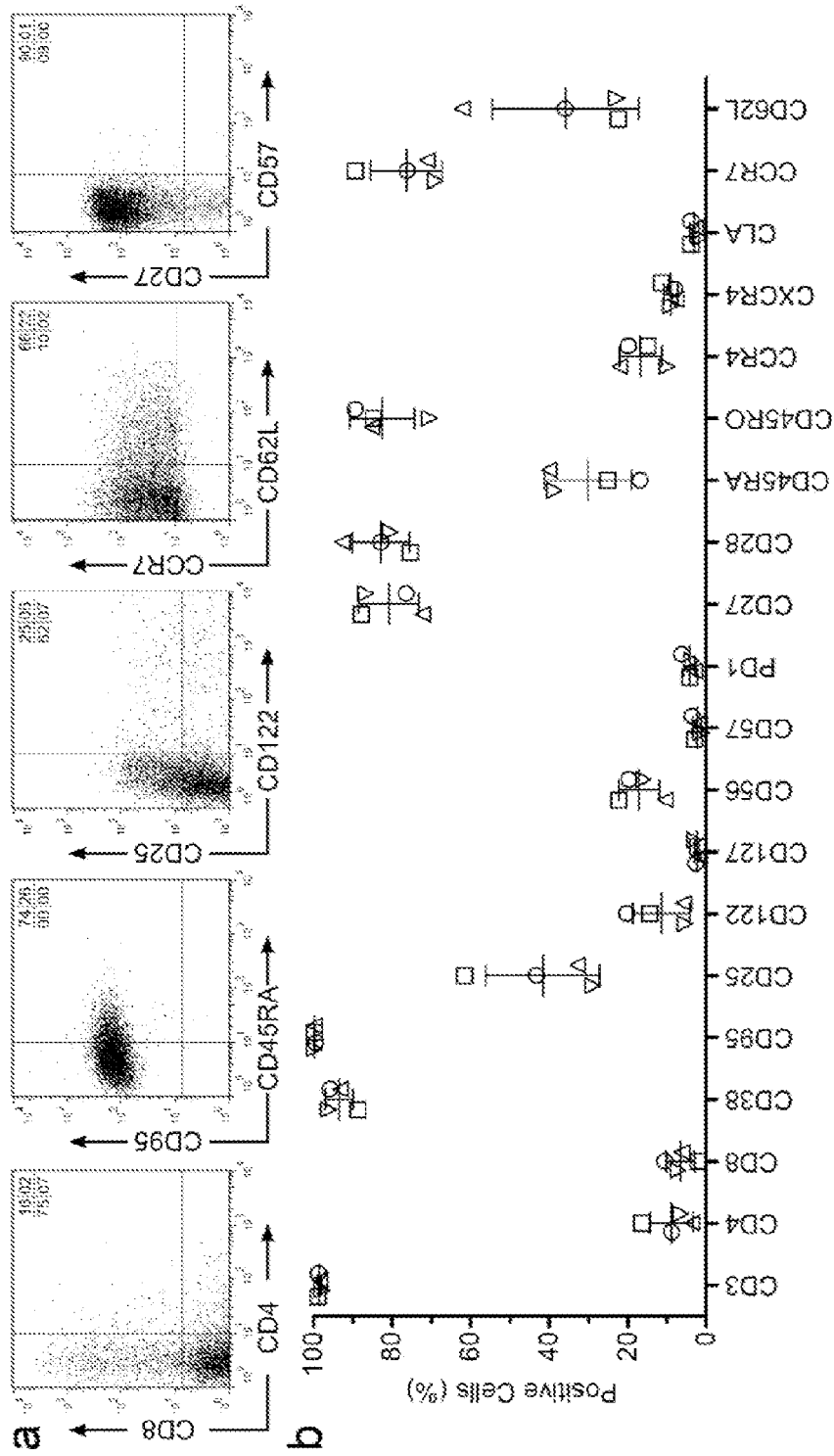
FIGS. 9A-B. Immunophenotype of polyclonal γδ T cells propagated on aAPC with IL-2 and IL-21. (A) Gating (one representative of four donors is shown from 2 independent experiments) and (B) frequency of surface makers by flow cytometry of PBMC-derived polyclonal γδ T cells at Day 22 of culture. Lines show mean±SD (n=4) pooled from two independent experiments where each symbol represents an individual donor.

T-cell functions, such as memory, homing, and cytolysis, can be predicted by their surface phenotype. The inventors explored a panel of markers to characterize the polyclonal γδ T cells (FIG. 9). After 22 days of co-culture on aAPC, most, but not all, γδ T cells were CD4$^{neg}$CD8$^{neg}$. These T cells were activated as measured by expression of CD38 and CD95, but not exhausted as evidenced by the absence of expression of CD57 and programmed death-1 (PD-1). Most cells expressed CD27 and CD28 co-stimulatory ligands and had a preference towards the antigen-experienced (CD45RO) over nave (CD45RA) markers. Their potential for homing to the skin, lymph nodes, and bone marrow was demonstrated by expression of CCR4, CCR7/CD62L, and CXCR4/CLA, respectively. These data are consistent with ability of aAPC to propagate γδ T cells that were activated and antigen experienced with potential for memory formation and homing to tissues.

Figure 10:
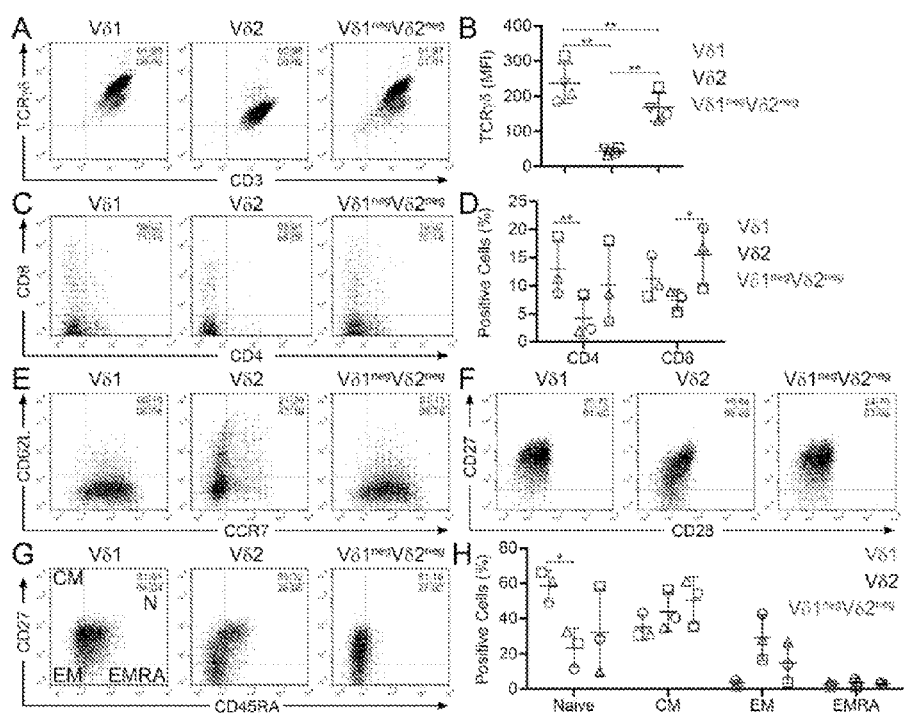
FIGS. 10A-H. Immunophenotype of Vδ T-cell subsets propagated on aAPC, IL-2, and IL-21. The Vδ1, Vδ2, and Vδ1$^{neg}$Vδ2$^{neg}$ subsets were analyzed after 15 days of proliferation as separated populations. (A) Flow cytometry plots of CD3 (x-axes) and TCRγδ (y-axes) expression in Vδ1, Vδ2, and Vδ1$^{neg}$Vδ2$^{neg}$ subsets (from left to right). (B) Mean fluorescence intensity (MFI) of TCRγδ staining in Vδ1 (red), Vδ2 (black), and Vδ1$^{neg}$Vδ2$^{neg}$ (blue) T-cell subsets where each shape represents a different donor and data are mean±SD (n=4) pooled from two independent experiments. (C) Representative flow cytometry plots of CD4 (x-axes) and CD8 (y-axes) expression on Vδ1, Vδ2, and Vδ1$^{neg}$Vδ2$^{neg}$ subsets (from left to right) and (D) summary of frequencies in Vδ1 (red), Vδ2 (black), and Vδ1$^{neg}$Vδ2$^{neg}$ (blue) T cells where data are mean±SD (n=3) pooled from two independent experiments and each shape represents a different donor. Flow cytometry plots of (E) CCR7 (x-axes) and CD62L (y-axes), (F) CD28 (x-axes) and CD27 (y-axes), and (G) CD45RA (x-axes) and CD27 (y-axes) expression in Vδ1, Vδ2, and Vδ1$^{neg}$Vδ2$^{neg}$ subsets (from left to right). (H) Assignment of γδ T cells to differentiation states based on expression of CD27 and CD45RA, as indicated in part (G). Each shape represents a different donor and data are mean±SD (n=3) pooled from two independent experiments. All flow plots are representative of four normal donors from two independent experiments. Quadrant frequencies (percentage) of flow plots are displayed in upper right corners.
Figure 11:
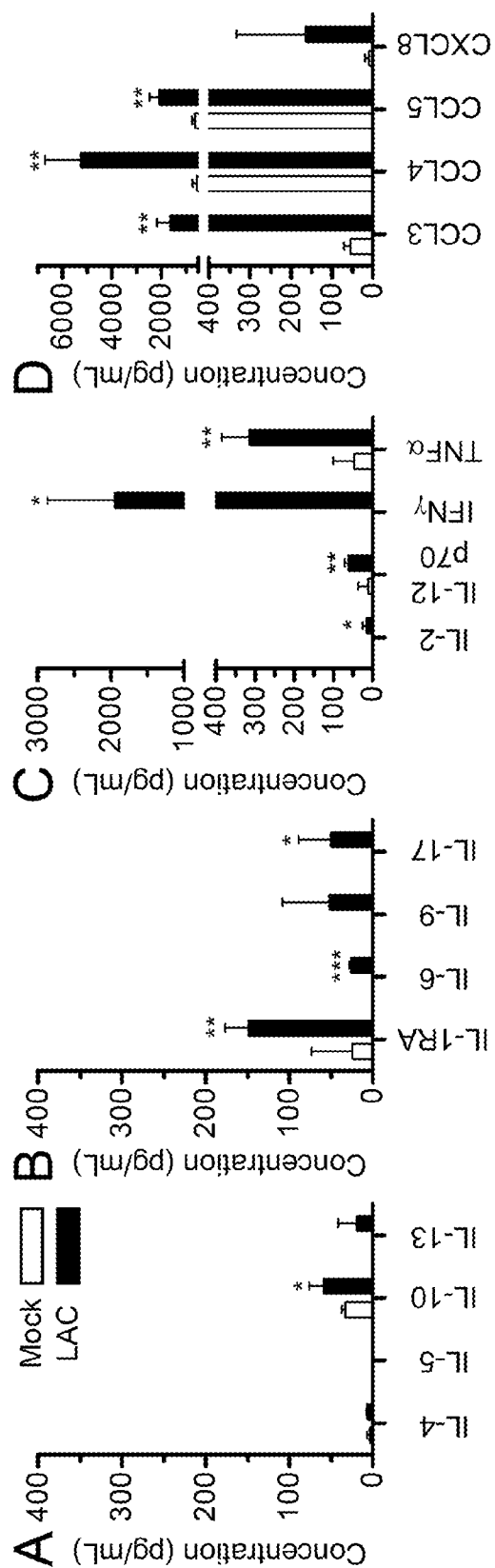
FIGS. 11A-D. Cytokines and chemokines secreted by polyclonal γδ T cells. At Day 22 of co-culture on γ-irradiated aAPC clone #4 with IL-2 and IL-21, T cells were incubated with CM (mock) or leukocyte activation cocktail (LAC; PMA/Ionomycin) for 6 h at 37° C. Tissue culture supernatants were interrogated using 27-Plex LUMINEX® array to detect presence of (A) TH2 cytokines, (B) TH17 cytokines, (C) TH1 cytokines, and (D) chemokines. Data are mean±SD pooled from four donors in two independent experiments where each donor had triplicate experimental wells pooled prior to multiplex analysis. Student's t-test performed for statistical analysis between mock and LAC groups for each cytokine or chemokine. *p<0.05, p<0.01, and *p<0.001

The inventors' approach to propagation enabled them to distinguish between Vδ1, Vδ2, and Vδ1$^{neg}$Vδ2$^{neg}$ lineages, and thus they investigated whether sub-populations of γδ T cells may have distinct differences in expression of markers that predict for their therapeutic potential. The inventors noted that the intensity of mAb staining for TCRγδ identified populations with distinct MFI (FIG. 1A). The Vδ2 T cells corresponded to the TCRγδ$^{low}$ grouping (43±9; mean±SD; n=4), Vδ1$^{neg}$Vδ2$^{neg}$ T cells corresponded to the TCRγδ$^{intermediate}$ grouping (168±40), and Vδ1 T cells corresponded to the TCRγδ$^{hi}$ grouping (236±56) (FIGS. 10A and 10B). CD4 and CD8 are not commonly expressed on γδ T cells, but variations were detected in expression of CD4 and CD8 in the separated subsets (FIGS. 10C and 10D). Differences were observed in expression of canonical markers used to describe memory among αβ T cells, including CCR7/CD62L (FIG. 10E) and CD27/CD28 (FIG. 10F) that showed Vδ1 and Vδ1$^{neg}$Vδ$^{neg}$ populations as distinct from Vδ2 cells. However, human γδ T-cell memory has been reported based on expression of CD27 and CD45RA (FIG. 10G) where CD27$^+$CD45RA$^+$, CD27$^+$CD45RA$^{neg}$, CD27$^{neg}$CD45RA$^{neg}$, and CD27$^{neg}$CD45RA$^+$ correspond to $T_N$, $T_{CM}$, $T_{EM}$, and $T_{EMRA}$, respectively (Caccamo et al., 2011; Pang et al., 2012). Most $T_N$ cells were Vδ1, most $T_{CM}$ were Vδ1$^{neg}$Vδ2$^{neg}$, most $T_{EM}$ cells were Vδ2, and all Vδ subsets had at least some $T_N$, $T_{CM}$, and $T_{EM}$ populations. In contrast, virtually no $T_{EMRA}$ were detected in any of the Vδ subsets (FIGS. 10G and 10H). Given these different immunophenotypes, the inventors propose that different functional attributes might be attributed to the three γδ T-cell subsets.

γδ T-Cell Subset Predicts Interferon-γ Produced in Response to Tumor.

γδ T cells can produce cytokines in response to activation. Therefore, a multiplex analysis of cytokines and chemokines was performed to determine whether aAPC-propagated γδ T cells would foster an inflammatory environment during therapy. Phorbol myristate acetate (PMA) and ionomycin were used as leukocyte activation cocktail (LAC) to mimic TCR activation. Cells mock-activated with media served as negative control. No significant production of $T_H2$ cytokines IL-4, IL-5, and IL-13 was observed from LAC-treated γδ T cells but there was a small increase in IL-10 production from baseline (FIG. 11A). In contrast, IL-1RA, IL-6, and IL-17 were significantly secreted by LAC-treated γδ T cells consistent with a $T_H17$ inflammatory response (FIG. 11B). Moreover, the pro-inflammatory $T_H1$ cytokines IL-2, IL-12 (p70), interferon-γ (IFNγ), and tumor necrosis factor-α (TNFα) were significantly produced by γδ T cells upon exposure to LAC compared to mock-treated controls (FIG. 11C). The chemokines CCL3 (macrophage inflammatory protein-1α; MIP1α), CCL4 (MIP1β), and CCL5 (regulated on activation, normal T cell expressed and secreted; RANTES) were detected in abundance (FIG. 11D). CCR5 binds to all three of these chemokines (Rostene et al., 2007), but only 6%±2% (mean±SD; n=4) of γδ T cells expressed this receptor. In aggregate, non-specific activation of γδ T cells led to a largely pro-inflammatory response, as desired for cell-based immunotherapies.

Figure 12:
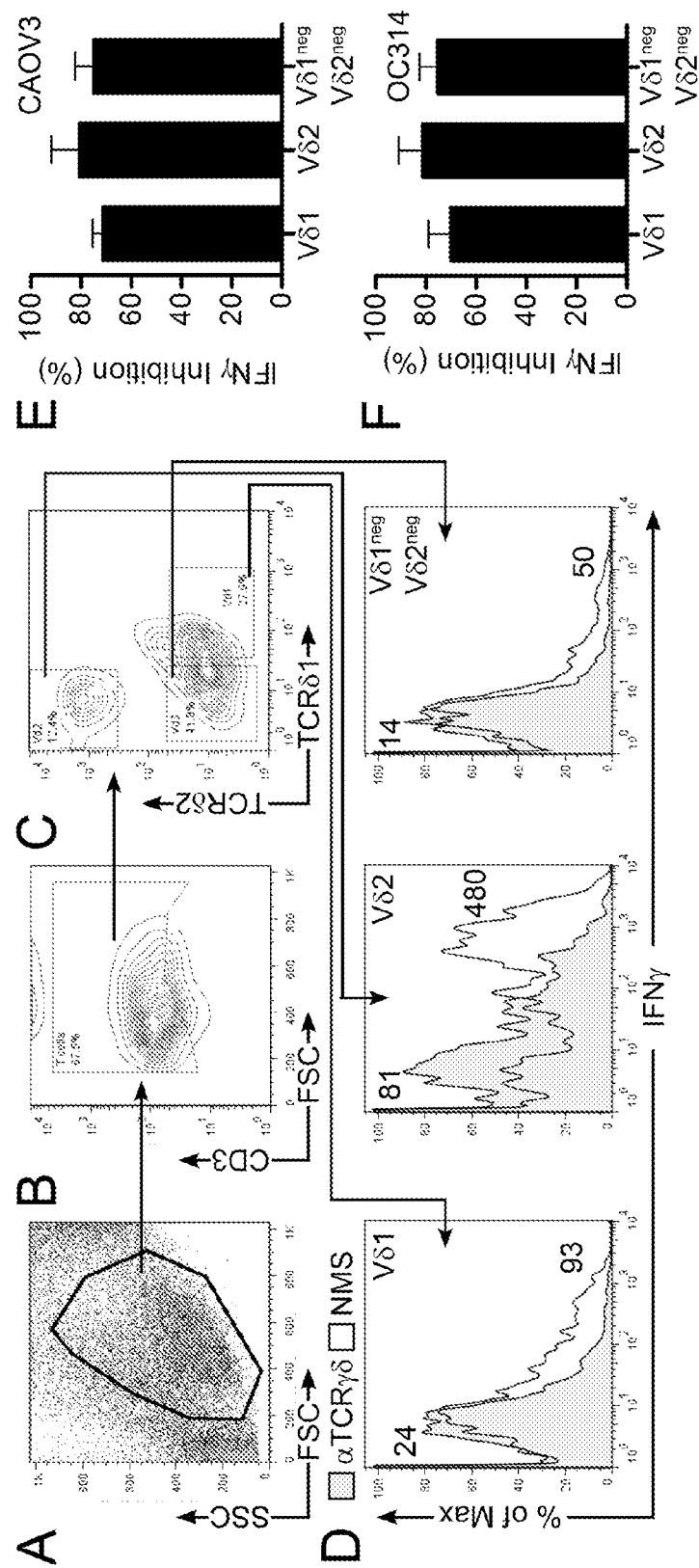
FIGS. 12A-F. Dependence on TCRγδ for IFNγ secretion in response to tumor cells. Polyclonal γδ T cells were incubated for 1 hour prior to and during 6 hour tumor cell co-culture with NMS (negative control) or neutralizing TCRγδ antibody (αTCRγδ; clone IM). Cells were stained for TCRδ1, TCRδ2, CD3, and IFNγ to gate T-cell subsets and assess IFNγ production. The gating strategy was (A) separation of forward and side scatter (FSC and SSC, respectively) in activated T-cell gate, (B) isolation of CD3$^+$ T cells from contaminating tumor cells in T-cell gate, and (C) separation into Vδ1, Vδ2, and Vδ1$^{neg}$Vδ2$^{neg}$ subsets based on TCRδ1$^+$TCRδ2$^{neg}$, TCRδ1$^{neg}$TCRδ2$^+$, and TCRδ1$^{neg}$TCRδ2$^{neg}$, respectively. (D) Comparisons of histograms detailing Vδ1, Vδ2, and Vδ1$^{neg}$Vδ2$^{neg}$ gates (from left to right) co-cultured with CAOV3 ovarian cancer cells and treated with NMS (open) or αTCRγδ (shaded). Numbers next to histograms are MFI. Flow plots are representative of one of three PB donors co-cultured with CAOV3 cells in two independent experiments. Percent inhibition of IFNγ secretion in response to (E) CAOV3 and (F) OC314 cells was calculated for each Vδ T-cell subset based on the following equation. Inhibition (%)=100−100×[(MFI$_{TUMOR+T\ CELL}$−MFI$_{T\ CELL\ ONLY}$)$_{αTCRγδ}$/(MFI$_{TUMOR+T\ CELL}$−MFI$_{T\ CELL\ ONLY}$)$_{NMS}$]. Data are mean±SD (n=3) pooled from two independent experiments.

IFNγ was the most responsive of all the assessed cytokines (FIG. 11C) and was chosen as a marker for γδ T-cell response to tumor. Intracellular cytokine expression was used to separate Vδ T cell subsets by flow cytometry and assess their response to tumors (FIGS. 12A-C). Co-culture of aAPC-propagated/activated polyclonal γδ T cells with ovarian cancer cells resulted in a hierarchy of IFNγ production following Vδ2>Vδ1>Vδ1$^{neg}$Vδ2$^{neg}$ as shown by IFNγ MFI of 855±475, 242±178, and 194±182 (mean±SD; n=4), respectively (FIG. 12D). The production of IFNγ was blocked with TCRγδ neutralizing antibody, suggesting that this cytokine response to the tumor was mediated through TCRγδ in each of the γδ T-cell subsets (FIGS. 12D-F). These data support the premise that the cytokine response was dependent on the γδ T cell subtype as identified by its TCRγδ.

Polyclonal γδ T Cells and Vδ T Cell Subsets Lyse a Broad Range of Tumor Cells.

Figure 13:
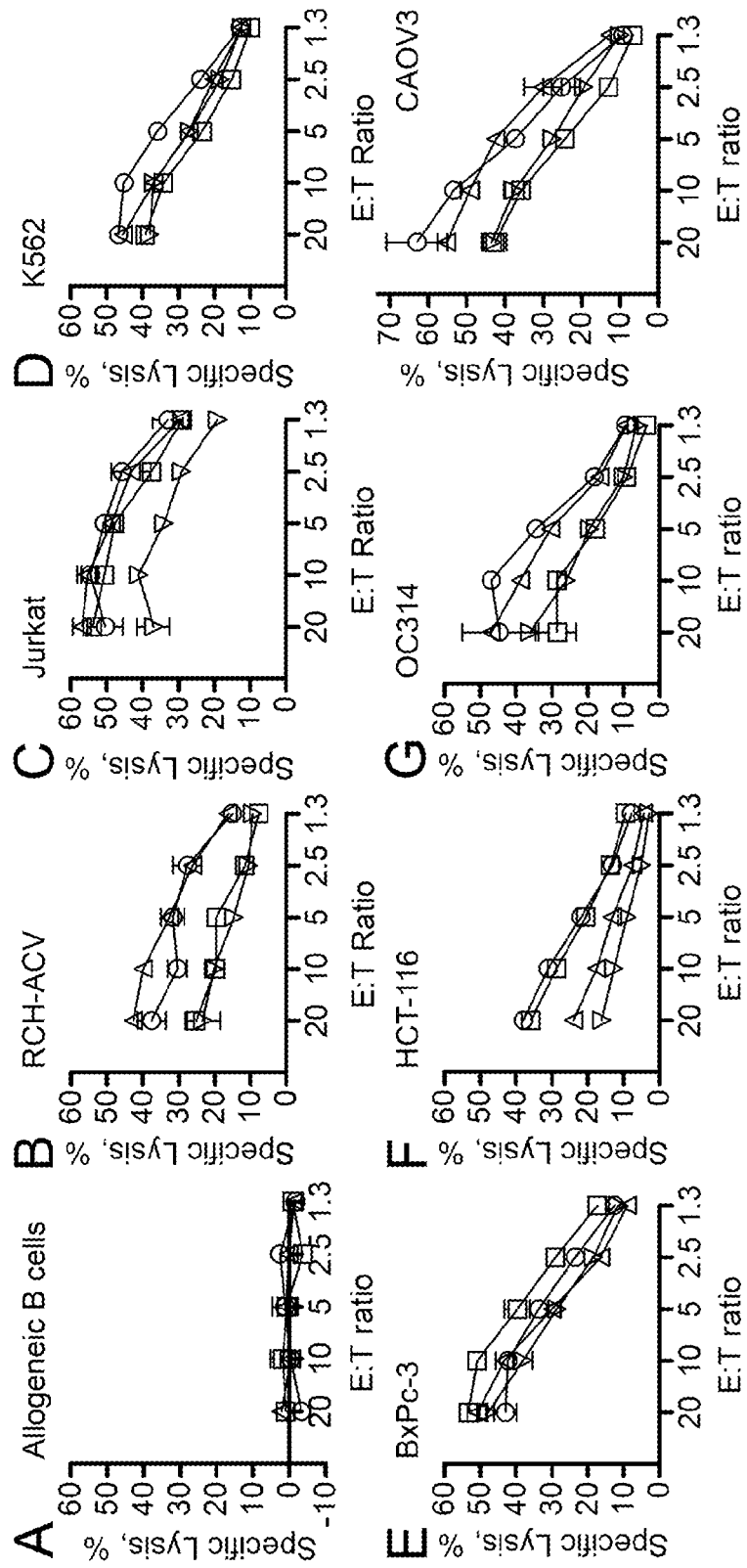
FIGS. 13A-G. Specific lysis of tumor cell line panel by polyclonal γδ T cells. Standard 4-h CRA was performed with increasing effector (polyclonal γδ T cells) to target (E:T) ratios against (A) B cells from an allogeneic donor (one of four representative donors), (B) B-ALL cell line: RCH-ACV, (C) T-ALL cell line: Jurkat, (D) CML cell line: K562, (E) pancreatic cancer cell line: BxPc-3, (F) colon cancer cell line: HCT-116, and (G) ovarian cancer cell lines: OC314 and CAOV3. Each line represents an individual PB donor of effector polyclonal γδ T cells where data are mean±SD (n=3 wells per assay) from two independent experiments.
Figure 14:
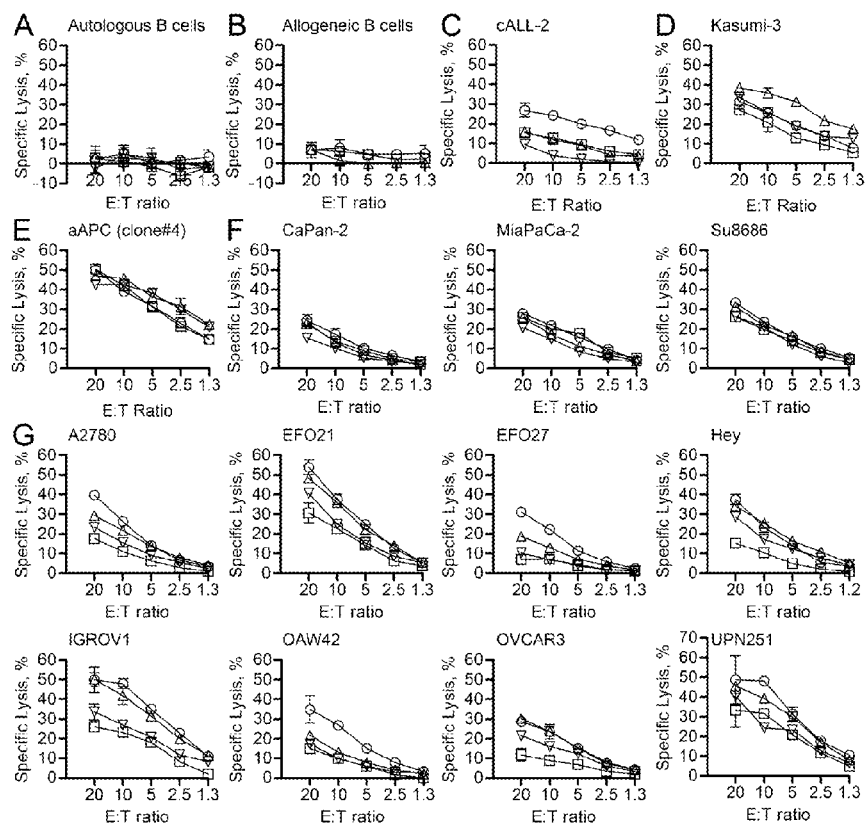
FIGS. 14A-G. In vitro lysis of tumor cell line panel by polyclonal γδ T cells. Standard 4-h CRA were performed with increasing effector (polyclonal γδ T cells) to target (E:T) ratios against (A) autologous B cells, (B) allogeneic B cells (1 of 4 donors), (C) B-ALL cell line: cALL-2, (D) undifferentiated leukemia cell line: Kasumi-3, (E) K562-derived aAPC clone #4, (F) pancreatic cancer cell lines: CaPan-2, MiaPaCa-2, and Su8686, and (G) ovarian cancer cell lines: A2780, EFO21, EF027, Hey, IGROV1, OAW42, OVCAR3, and UPN251. Each line represents an individual γδ T-cell population (derived from a PB donor) and lysis data are presented as mean±SD (n=3 wells per assay) pooled from two independent experiments.

After establishing that aAPC-propagated/activated γδ T cells could be activated to produce pro-inflammatory mediators, the inventors examined their ability to lyse a broad range of tumor cell lines (FIGS. 13 and 14). Polyclonal γδ T cells displayed virtually no cytolysis against autologous or allogeneic normal B cells, but were able to kill allogeneic B-cell acute lymphoblastic leukemia (ALL) cell lines RCH-ACV and cALL-2. T-cell ALL cell line Jurkat was also sensitive to cytolysis, suggesting that γδ T cells could be used to target both B-cell and T-cell malignancies. Kasumi-3 is a CD33$^+$CD34$^+$ undifferentiated leukemia cell line that was killed by γδ T cells, which supports targeting minimally differentiated tumors with γδ T cells. The chronic myelogenous leukemia (CML) cell line K562 and K562-derived clone #4 aAPC were killed by polyclonal γδ T cells. Pancreatic cancer cell lines, BxPc-3, CaPan-2, MiaPaCa-2, and Su8686, were lysed by γδ T cells, as was the colon carcinoma cell line HCT-116. Ten ovarian cell lines were killed by polyclonal γδ T cells in the following order of decreasing sensitivity: CAOV3>EFO21>UPN251>IGROV1>OC314>Hey>A2780>OVCAR3>OAW42>EFO27. These cytolysis data highlight the ability of allogeneic polyclonal γδ T cells to specifically kill a broad range of tumors in vitro.

Figure 15:
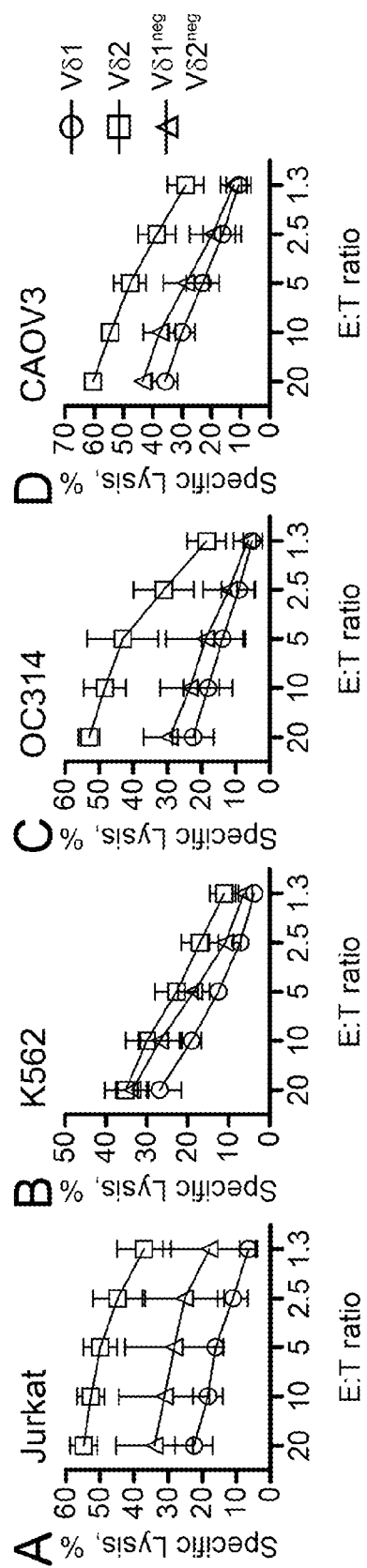
FIGS. 15A-D. Specific lysis of hematological and solid tumor cells by Vδ T-cell subsets. Standard 4-h CRA with Vδ1 (circles), Vδ2 (squares), and Vδ1$^{neg}$Vδ2$^{neg}$ (triangles) γδ T-cell subsets effectors targeting (A) Jurkat, (B) K562, (C) OC314, and (D) CAOV3 cancer cell lines. Data were pooled from two independent experiments and are mean±SD (n=4) of donor averages from triplicate measurements in CRA.
Figure 16:
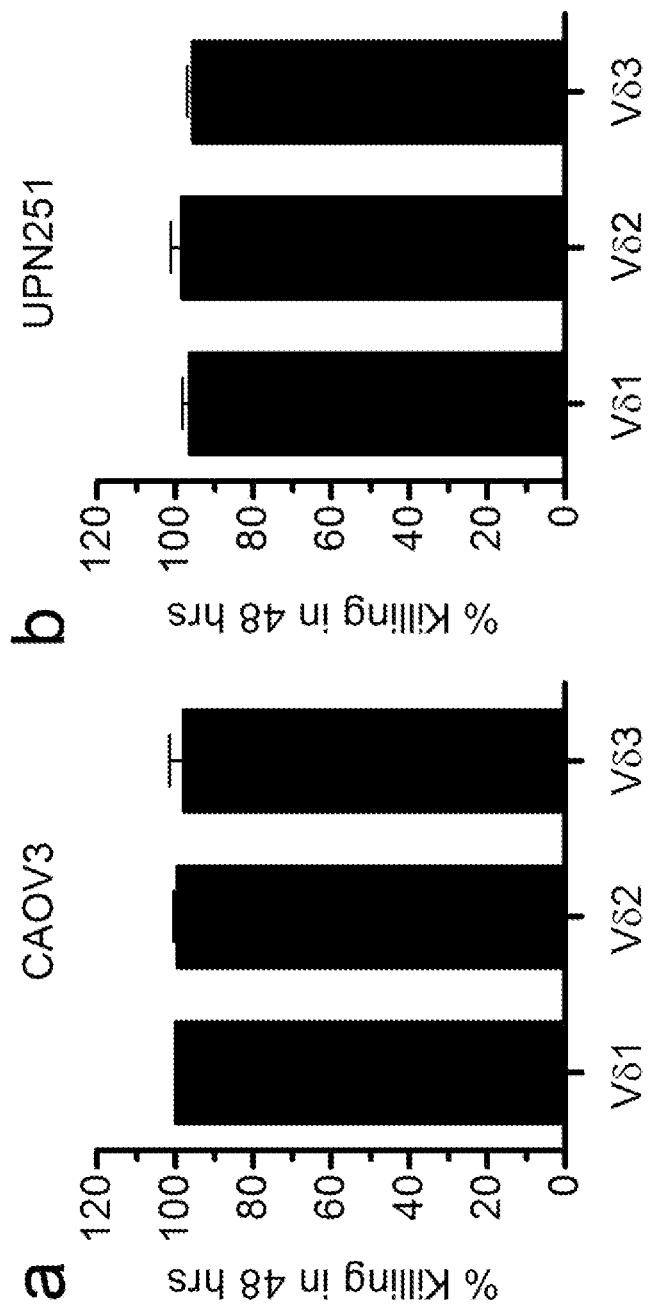
FIGS. 16A-B. Long-term killing potential by γδ T-cell subsets. (A) CAOV3 and (B) UPN251 ovarian tumor cells were seeded in 6-well plates and incubated overnight to establish adherence. T cells from Vδ1, Vδ2, or Vδ1$^{neg}$Vδ2$^{neg}$ subsets were then co-cultured with tumor cells for two days. Remaining adherent cells were enzymatically removed from the wells and counted for viable cells. Tumor cells without T cells served as the positive control and T cells without tumor cells served as the negative control. Killing (%)=(Viable cells)$_{Co-culture}$/(Viable cells)$_{Tumor\ only}$×100. Data are mean±SD (n=3) pooled from three independent experiments.

The inventors next determined the killing potential of the three separated γδ T-cell populations. Hematological (Jurkat) and K562 and solid (OC314 and CAOV3) tumor cell lines were lysed by all three Vδ lineages (FIG. 15). A distinct order of lysis was observed for all targets with the ranking Vδ2>>Vδ1$^{neg}$Vδ2$^{neg}$>Vδ1 defining the killing potential in 4-h assays (FIG. 15). This was consistent with the T-cell differentiation immunophenotype as the frequency of $T_{EM}$ cells followed $V\delta2 > V\delta1^{neg}V\delta2^{neg} > V\delta1$ (FIG. 10H) and $T_{EM}$ cells have been reported to possess higher effector potential relative to less differentiated T cells (June, 2007). Long-term assays were undertaken to assess killing after 48 h of co-culture between the Vδ subsets and tumor cells (FIG. 16). Greater than 95% of CAOV3 and UPN251 tumor cells were eliminated by all three subsets within two days. Collectively, these data established that each Vδ lineage propagated on aAPC was capable of lysing tumor, albeit with different efficiencies, and anti-tumor activity of the $V\delta^{neg}V\delta2^{neg}$ sub-population was observed for the first time.

Figure 17:
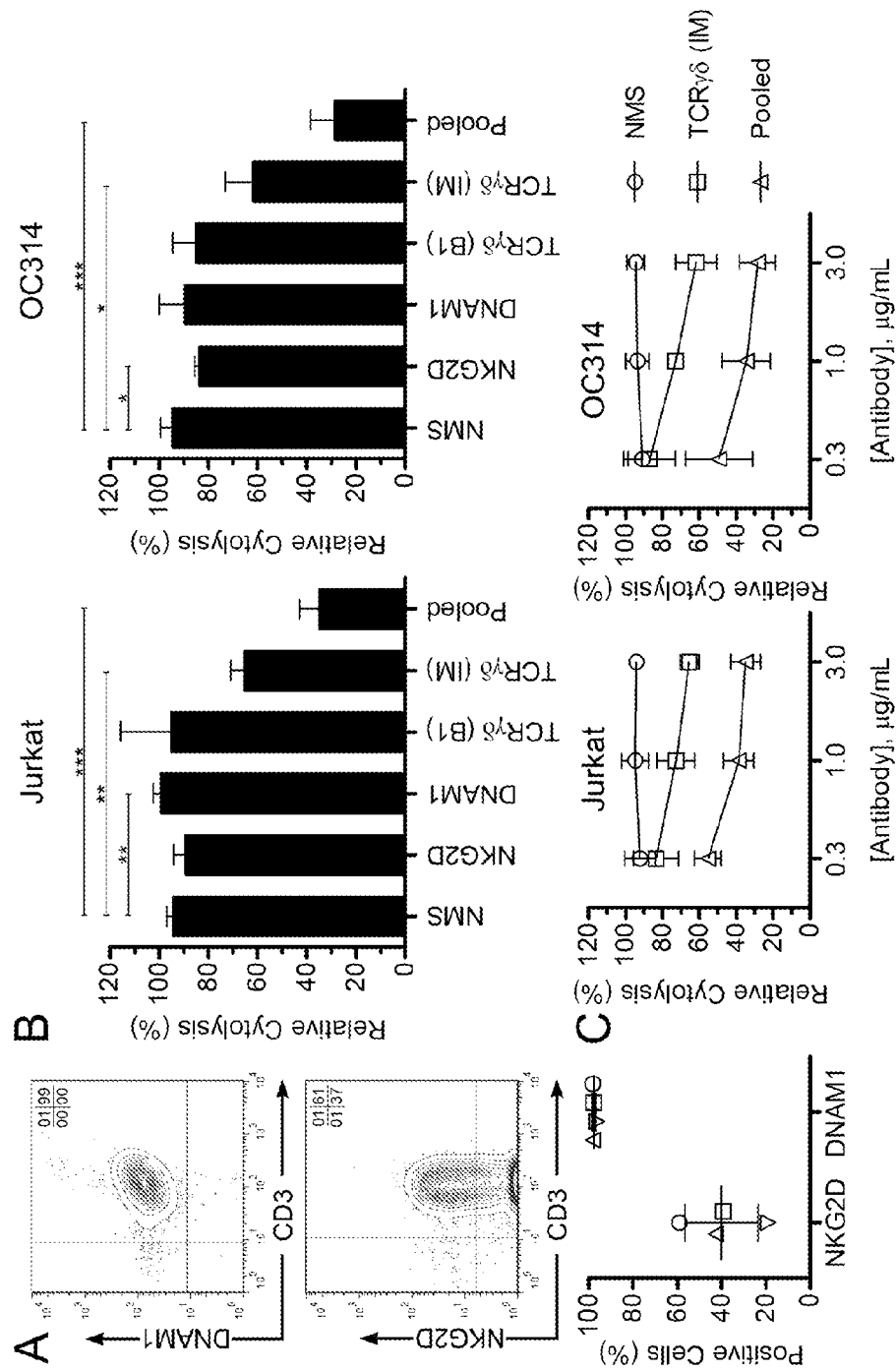
FIGS. 17A-C. Inhibition of tumor lysis by polyclonal γδ T cells. (A) Representative expression of CD3, DNAM1, and NKG2D on polyclonal γδ T cells from PB after 22 days of propagation on aAPC clone #4 in presence of IL-2 and IL-21. One of four donors from two independent experiments is displayed. Quadrant frequencies of flow plots are displayed in upper right corner of each plot. Cumulative frequencies (percentage) are displayed as mean±SD (n=4) where each shape represents a different donor. (B) Neutralizing antibodies to NKG2D, DNAM1, TCRγδ (clone B1), and TCRγδ (clone IM) were used to block killing of Jurkat (left) or OC314 (right) tumor targets at an E:T ratio of 12:1 in standard 4-h CRA. Antibodies were pre-incubated with T cells for 1 h and during CRA at 3 μg/mL. NMS served as control for addition of antibody and wells without antibody were used for normalization purposes. Specific lysis was normalized to wells without antibody to yield relative cytolysis as defined by: Relative cytolysis (%)=(Specific Lysis)$_{With\ Antibody}$/(Specific Lysis)$_{Without\ Antibody}$×100. Data are mean±SD (n=4 donors) from triplicate normalized CRA measurements pooled from two independent experiments. Two-way ANOVA with Bonferroni's post-tests was used for statistical analysis. *p<0.05, p<0.01, and *p<0.001 (C) Dose-dependent inhibition by NMS (circles), TCRγδ IM antibody (squares), or pooled (triangles) antibodies (specific for DNAM1, NKG2D, TCRγδ (B1), and TCRγδ (IM)) of cytolysis of Jurkat (left) and OC314 (right) cells by polyclonal γδ T cells with antibodies at 0.3, 1, and 3 μg/mL. Data are mean±SD (n=4 donors) from triplicates pooled and normalized from two independent experiments.

Efficiency of tumor lysis is influenced by TCRγδ, NKG2D, and DNAM1. The inventors sought to determine if cytolysis by T cells was directly dependent upon the TCRγδ by blocking receptors with antibodies. The experimental approach took into account that γδ T cells co-express DNAM1 and NKG2D (FIG. 17A), which can activate both T cells and NK cells for killing (Bauer et al., 1999; Gilfillan et al., 2008). Antibodies specific for NKG2D, DNAM1, and TCRγδ (clone B1) had minimal impact on reducing lysis of Jurkat and OC314 cells. In contrast, antibody blocking TCRγδ (clone IM) reduced killing of both Jurkat and OC314 cells (FIG. 17B). A pool of antibodies (binding NKG2D, DNAM1, TCRγδ) resulted in further reduction, in a dose-dependent manner, of γδ T-cell mediated cytolysis of Jurkat (reduction of 65%±8%) and OC314 (reduction of 71%±10%) cells (FIGS. 17B and 17C). In aggregate, these results demonstrated that activation of aAPC-propagated/activated γδ T cells for killing is multi-factorial, but dependent on TCRγδ.

Established Ovarian Cancer Xenografts are Eliminated by Adoptive Transfer of γδ T Cells.

Figure 18:
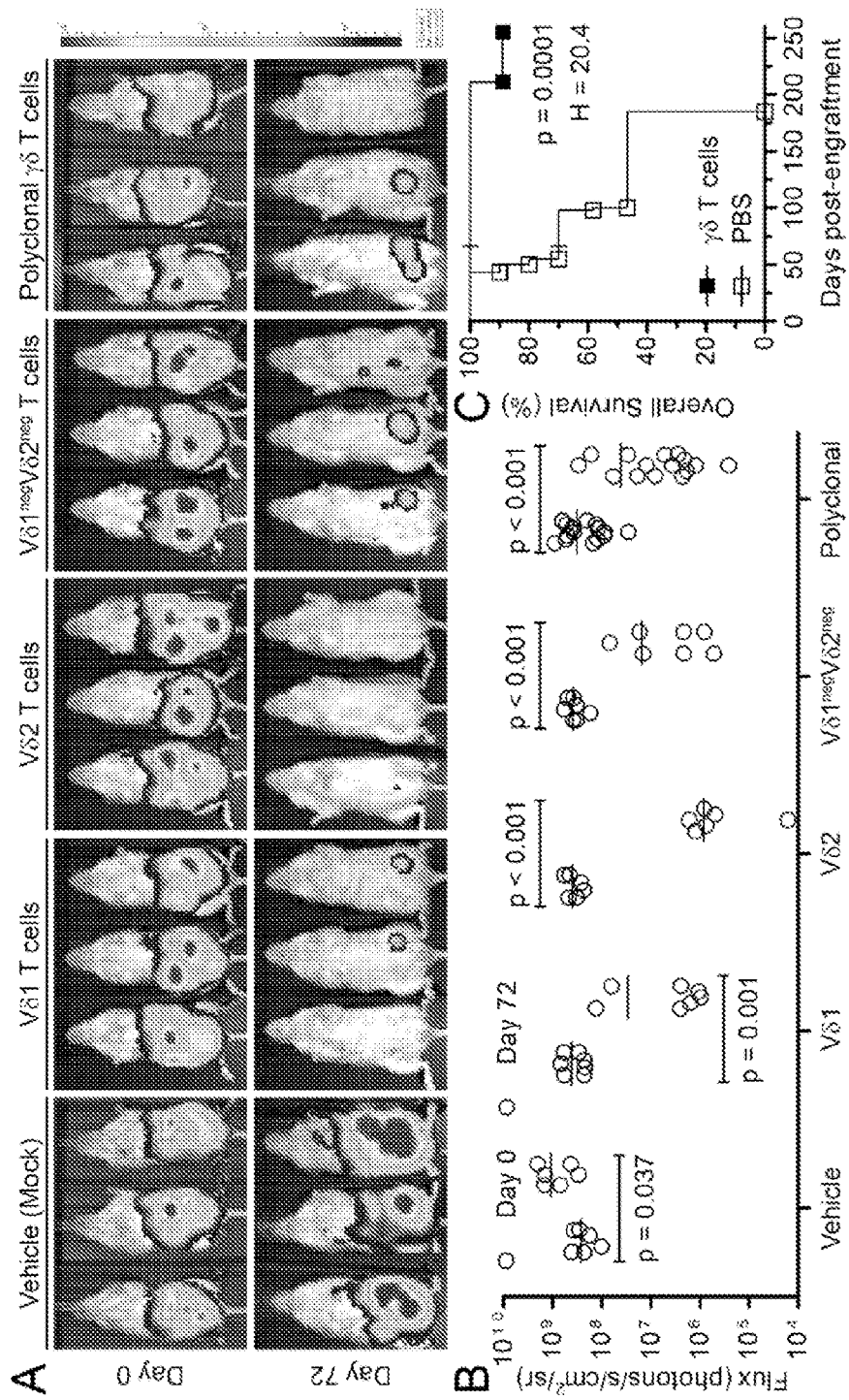
FIGS. 18A-C. In vivo clearance of ovarian cancer upon adoptive transfer of polyclonal γδ T cells and γδ T-cell subsets propagated/activated on aAPC with IL-2 and IL-21. CAOV3-effLuc-mKate tumor cells (3×10$^6$ per mouse) were injected i.p. into NSG mice at Day −8 and engrafted until Day 0 when treatment was started with either PBS (vehicle/mock) or γδ T cells. Four T-cell doses were administered i.p. with 3×10$^6$, 6×10$^6$, 10×10$^6$, and 15×10$^6$ cells on days 0, 7, 14, and 21, respectively. (A) BLI images at Day 0 (top panels) or Day 72 (bottom panels) in vehicle, Vδ1, Vδ2, Vδ1$^{neg}$Vδ2$^{neg}$, and polyclonal γδ T-cell treatment groups. Images are representative of 6-14 mice from two independent experiments. (B) BLI measurements of mice at Day 0 (black) and Day 72 (blue) where each shape represents an individual mouse, lines are mean (n=6-14), and data are pooled from two independent experiments. Student's paired, 2-tailed t-tests were used for statistical analysis and p values are displayed. (C) Overall survival of mice treated with vehicle (open squares) or polyclonal γδ T cells (solid squares). Gehan-Breslow-Wilcoxon Test was used to calculate p value. H=hazard ratio.

The adoptive transfer of aAPC-propagated/activated polyclonal γδ T cells is proposed as immunotherapy for human cancer. To model this, NSG mice received an intraperitoneal (i.p.) injection of CAOV3-effLuc-mKate ovarian cancer cells and were then randomized into treatment groups. Following eight days of engraftment, either vehicle, Vδ1, Vδ2, $V\delta1^{neg}V\delta2^{neg}$, or polyclonal γδ T cells were administered (escalating doses) i.p. to mice (FIG. 18). Tumor burden was serially monitored during the experiment with non-invasive bioluminescence imaging (BLI). Established tumors (FIGS. 18A top panels and 18B) continued to grow in vehicle (mock) treated mice, but were significantly reduced in mice treated with the Vδ1 (p=0.001), Vδ2 (p<0.001), $V\delta1^{neg}V\delta2^{neg}$ (p<0.001), and polyclonal (p<0.001) γδ T cells (FIGS. 18A bottom panels and 18B). Treatment with polyclonal γδ T cells improved overall survival (p=0.0001) compared to mock-treated mice where 90% of mice survived ovarian cancer xenograft and hazard ratio for mice without treatment was 20.4 (FIG. 18C). This is the first time that the three Vδ subsets have been compared for their ability to target tumor in vivo and is the first evaluation of $V\delta1^{neg}V\delta2^{neg}$ T cells in regards to in vivo anti-tumor activity. In sum, γδ T cells were effective in treating cancer in vivo and thus represent an attractive approach to cell-based cancer treatment.

Example 2—Materials and Methods

Cell Lines and Cell Culture.

HCT-116 (cat #CCL-247), Kasumi-3 (cat #CRL-2725), and K562 (cat #CCL-243) cell lines were acquired from American Type Culture Collection (ATCC; Manassas, Va.). Jurkat (cat #ACC 282) cell line was received from Deutsche Sammlung von Mikroorganismen and Zellkulturen (DSMZ; Germany). K562-were genetically modified to function as aAPC (clone #4) as previously described (Manuri et al., 2010; Singh et al., 2011). B-cell acute lymphoblastic leukemia (B-ALL) cell lines cALL-2 and RCH-ACV cell lines were gifts from Dr. Jeff Tyner (OHSU), pancreatic cancer cell lines (BxPC-3, CaPan-2, MiaPaCa-2, and Su8686) were donated by Dr. Viji Ramachandran (MDACC), and ovarian cancer cell lines (A2780, CAOV3, EFO21, EF027, Hey, IGROV1, OAW42, OC314, OVCAR3, and UPN251) were provided by Dr. Robert C. Bast, Jr. (MDACC). Cell cultures were maintained in (i) RPMI (Gibco, Grand Island N.Y.): K562 parental cells, aAPC clone #4, aAPC clone A6, aAPC clone A3, aAPC clone D4, Jurkat, cALL-2, RCH-ACV, Kasumi-3, A2780, EFO21, EF027, Hey, IGROV1, OC314, OVCAR3, and UPN251, (ii) DMEM (Sigma, St. Louis, Mo.): 293-METR, CAOV3, BxPC-3, CaPan-2, MiaPaCa-2, OAW42, and Su8686, or (iii) McCoy's 5A (Sigma): HCT-116. Each media was supplemented with 10% heat-inactivated fetal bovine serum (Hyclone, Logan, Utah) and 1% GLUTAMAX®-100 (Gibco). UPN251 and OAW42 cells were supplemented with insulin-transferrin-selenium solution (Gibco). Cells were cultured under humidified conditions with 5% $CO_2$ at 37° C.

Propagation of γδ T Cells.

Peripheral blood mononuclear cells (PBMC) and umbilical cord blood (UCB) were isolated from healthy volunteers by Ficoll-Hypaque (GE Healthcare) after informed consent was granted (Singh et al., 2008). $10^8$ thawed PBMC were initially treated with CD56 microbeads (cat #130-050-401, Miltenyi Biotec, Auburn, Calif.) and separated on LS columns (cat #130-042-401, Miltenyi Biotec) to deplete NK cells from cultures. Unlabeled cells from CD56 depletion sorting were then labeled with TCRγ/δ+ T-cell isolation kit (cat #130-092-892, Miltenyi Biotec) and placed on LS columns to separate γδ T cells in the unlabeled fraction from other cells attached to magnet. γδ T cells were stimulated at a ratio of one T cell to two γ-irradiated (100 Gy) aAPC (clone #4) in the presence of exogenous IL-2 (Aldeleukin; Novartis, Switzerland; 50 U/mL, added three times per week beginning the day of aAPC addition) and IL-21 (cat #AF20021; Peprotech, Rocky Hill, N.J.; 30 ng/mL, added three times per week beginning the day of aAPC addition) in complete media (CM; RPMI, 10% FBS, 1% GLUTA-MAX®). Cells were serially re-stimulated with addition of aAPC every 7 days for 2-5 weeks in the presence of soluble cytokines. Validation of co-expression of CD19, CD64, CD86, CD137L, and eGFP (IL-15 peptide fused in frame to IgG4 Fc stalk and co-expressed with eGFP) on aAPC clone #4 was performed before addition to T-cell cultures (Singh et al., 2011). Fluorescence activated cell sorting (FACS) was used to isolate Vδ1 ($V\delta1^+V\delta2^{neg}$), Vδ2 ($V\delta1^{neg}V\delta2^+$), and $V\delta1^{neg}V\delta2^{neg}$ ($V\delta1^{neg}V\delta2^{neg}$) populations, which were stimulated twice as above with aAPC clone #4, phenotyped, and used for functional assays. UCB-derived γδ T cells were isolated by FACS from thawed mononuclear cells using anti-TCR-γδ and anti-CD3 mAbs and were stimulated for five weeks on aAPC/cytokines as per PBMC.

Co-Culture of γδ T Cells on aAPC.

Figure 2:
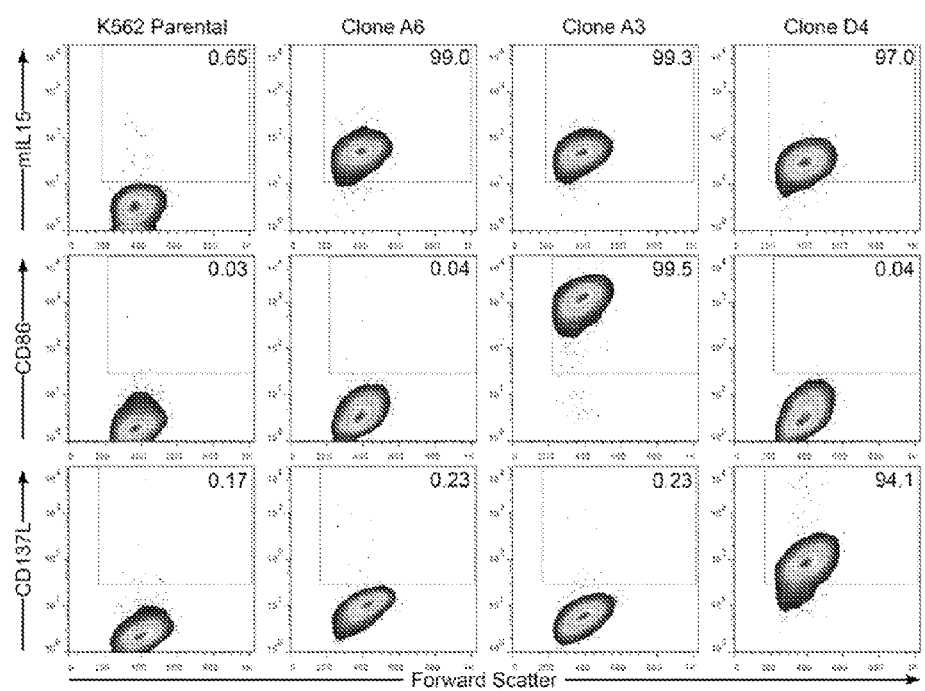
FIG. 2. aAPC developed for co-culture with γδ T cells to uncover the impact of introduced co-stimulatory molecules. K562 cells were electroporated with Sleeping Beauty (SB) transposase and SB transposon expressing a variant of membrane-bound IL-15 (mIL15), in which IL-15 cytokine/peptide is fused to IL-15 receptor-α. Genetically-modified cells were single-cell sorted by FACS to generate aAPC clone A6. Note that aAPC clone A6 uses a different variant of mIL15 than aAPC clone #4. Clone A6 was then electroporated with SB transposase and SB transposons containing either CD86 or CD137L and genetically modified cells were single cell sorted by FACS to generated aAPC clones A3 and D4. Cell surface immunophenotypes of aAPC are shown where forward scatter is displayed on x-axes and mIL15, CD86, and CD137L are displayed on top, middle, and bottom y-axes, respectively.

In order to assess the dependence of γδ T cells on cytokines for proliferation, co-cultures were initiated with $10^5$ γδ T cells and $2\times10^5$ aAPC (clone #4) then were added to an equal volume of (i) CM, (ii) CM and 100 U/mL IL-2, (iii) CM and 60 ng/mL IL-21, or (iv) CM, 100 U/mL IL-2, and 60 ng/mL IL-21. T cells were enumerated using a CELLOMETER® Auto T4 cell counter (Nexcelom, Lawrence, Mass.) nine days after initiating co-cultures to determine yields. K562 cells were genetically modified with one or more co-stimulatory molecules to generate three new aAPC (FIG. 2). A Sleeping Beauty (SB) transposon expressing IL-15 peptide fused in frame to IL-15Rα and SB11 transposase were co-electro-transferred into parental K562 cells (CD86$^{neg}$ and CD137L$^{neg}$) by nucleofection with NUCLEOFECTOR® II (Lonza, Basel, Switzerland) and Kit V (cat #VCA-1003, Lonza). FACS was used to isolate mIL15$^+$cells and establish a clone (designated clone A6; mIL15$^+$CD86$^{neg}$CD137L$^{neg}$) which was then electroporated with SB11 and SB transposons expressing CD86 or CD137L. Cells were FACS sorted again to obtain clones A3 (mIL15$^+$CD86$^+$CD137L$^{neg}$) and D4 (mIL15$^+$CD86$^{neg}$CD137L$^+$). Co-cultures were initiated with $10^5$ γδ T cells in CM supplemented with 100 U/mL IL-2 and 60 ng/mL IL-21 and were added to $2\times10^5$ γ-irradiated (i) parental K562 cells, (ii) clone A6, (iii) clone A3, (iv) clone D4, (v) clone #4 aAPC, or (vi) no aAPC. T cells were enumerated 9 days after initiating as described above for cytokine experiments.

Flow cytometry.

Cells were phenotyped with antibodies detailed in Table 1. Isotype controls were used to validate gating. Staining was performed in FACS buffer (phosphate-buffered saline, 2% fetal bovine serum, 0.1% sodium azide) for 20-30 min at 4° C., and two washes with FACS buffer were performed before staining and between stains. Intracellular staining was done following fixation and permeabilization for 20 min at 4° C. with BD CYTOFIX/CYTOPERM™ (BD Biosciences, San Diego, Calif.). Intracellular staining was performed in Perm/Wash buffer, 10% human AB serum for 30 min at 4° C. FITC, PE, PerCP/Cy5.5, and APC antibodies were used at 1:20, 1:40, 1:33, and 1:40 dilutions, respectively. Samples were acquired on FACSCalibur™ (BD Biosciences, San Jose, Calif.) and analyzed with FlowJo software (version 7.6.3).

Abundance and Identity of mRNA Molecules by DTEA.

At designated times after co-culture on aAPC, T cells were lysed at a ratio of 160 μL RLT Buffer (Qiagen) per $10^6$ cells and frozen at −80° C. RNA lysates were thawed and immediately analyzed using an NCOUNTER® Analysis System (NanoString Technologies, Seattle, Wash.) following a minimum of 12 h hybridization at 65° C. using multiplexed target-specific color-coded reporter and biotinylated capture probes to detect mRNAs of interest. Two CodeSets were generated from RefSeq accession numbers for selected mRNA transcripts and were used to generate the specific reporter and capture probe pairs for the designer TCR expression array (DTEA). Reporter-capture NCOUNTER® probe pairs were identified that (i) minimized off-target effects due to cross-hybridization of reporter-capture probe pairs to non-target molecules, (ii) target most, if not all, of the transcript variants for a particular gene, and (iii) efficiently hybridize. DTEA data was normalized to both spike positive control RNA and housekeeping genes (ACTB, G6PD, OAZ1, POLR1B, POLR2A, RPL27, Rps13, and TBP). Spiked positive control normalization factor was calculated from the average of sums for all samples divided by the sum of counts for an individual sample. Spiked positive control normalization factor was calculated from the average of geometric means for all samples divided by the geometric mean of counts for an individual sample. Normalized counts were reported.

Cytokine Secretion.

Expression of cytokines was assessed by intracellular staining and secretion of cytokines into tissue culture supernatants was evaluated by LUMINEX® multiplex analysis. For the former, γδ T cells were incubated with either normal mouse serum (NMS; Jackson ImmunoResearch) or TCRγδ blocking antibody (clone IMMU510 (IM); Thermo Fisher, Pittsburgh, Pa.) at 37° C. for 1 h at concentrations of 0.6, 2.0, and 6.0 ng/mL. T cells were then added to an equal volume and number of target cells (CAOV3 or OC314) to yield final antibody concentrations of 0.3, 1.0, and 3.0 ng/mL. Co-cultures were incubated for 6 h at 37° C. in the presence of Brefeldin-A (GolgiPlug; BD Biosciences) to block exocytosis and secretion of cytokines. Co-cultures were then (i) stained for surface markers, e.g., CD3, TCRδ1, and TCRδ2, (ii) fixed and permeabilized with BD CYTOFIX/CYTOPERM™ (cat #555028, BD Biosciences), (iii) stained for intracellular IFNγ, and (iv) analyzed by flow cytometry. Co-cultures to assess cytokine secretion were incubated for 24 h in CM (mock treatment) or leukocyte activation cocktail (LAC; 5 ng/mL PMA and 500 ng/mL Ionomycin) and supernatants from triplicate wells were pooled and analyzed by BIO-PLEX® Human Cytokine Group I 27-plex Assay (cat #L50-OKCAF0Y, BioRad Technologies, Hercules, Calif.) using LUMINEX® 100 (xMap Technologies, Austin, Tex.).

Chromium Release Assay.

In vitro specific lysis was assessed using a standard 4-h CRA, as previously described (Singh et al., 2011). B cells from healthy donors were isolated with CD19 microbeads (cat #130-050-301, Miltenyi Biotec) the day of each assay and used as target cells. Antibodies specific for NKG2D (clone 1D11; BD Biosciences), DNAM1 (clone DX11; BD Biosciences), TCRγδ (clone B1; BD Biosciences), and TCRγδ (clone IM) were used for neutralization experiments at 0.3, 1.0, and 3.0 ng/mL in CRA at E:T ratio of 12:1. NMS was used as a negative control at the same concentrations and wells without antibodies were used for purposes of data normalization.

Long-Term Killing Assays.

Adherent tumor cells (CAOV3 or UPN251) were seeded in 12-well plates at a density of $4\times10^4$ cells/well. The following day, $5\times10^5$ γδ T cells were added to each well and an equal number was added to a well without tumor cells (media only). One well of tumor cells had an equal volume of CM added as a positive control for growth. After 2 days, supernatants were harvested, wells were washed in PBS, and remaining tumor cells were harvested with trypsin-EDTA and enumerated. The abundance of tumor cells remaining were normalized to mock-treated tumor cells.

Lentivirus Packaging and Transduction of CAOV3 Cells.

Figure 19:
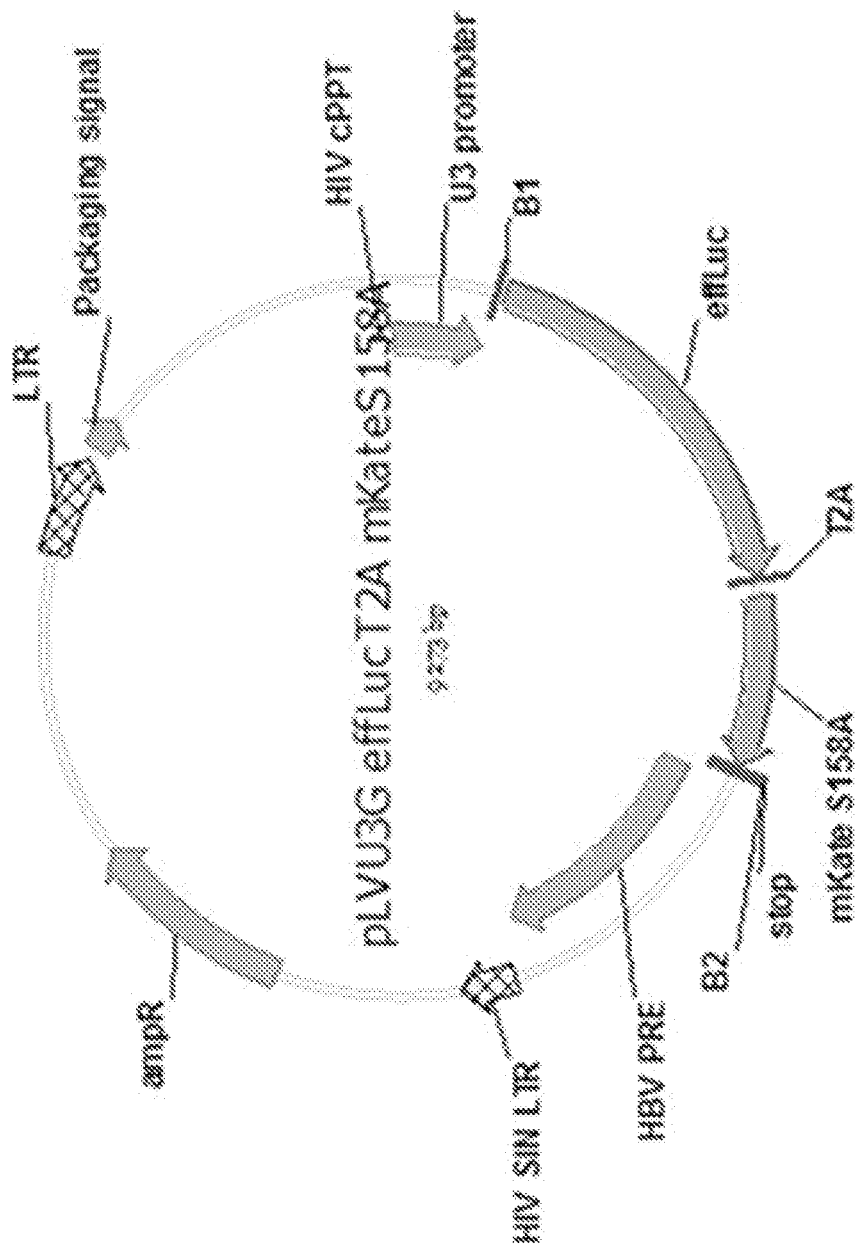
FIG. 19. Schematic of DNA plasmid pLVU3G-effLuc-T2A-mKateS158A used to co-express enhanced firefly luciferase (effLuc) and mKate. Annotations are, LTR: long terminal repeat; HIV cPPT: HIV central polypurine tract; B1: Gateway donor site B1; effLuc: enhanced firefly Luciferase; T2A: T2A ribosomal slip site; mKate S158A: enhanced mKate red fluorescence protein; B2: Gateway donor site B2; HBV PRE: Hepatitis B post-translational regulatory element; HIV SIN LTR: HIV self-inactivating long terminal repeat; ampR: ampicillin resistance ((3-Lactamase).

Lentivirus particles were packaged according to a modified version of a protocol described elsewhere (Turkman et al., 2011) to introduce enhanced firefly Luciferase (effLuc) into tumor cells for non-invasive imaging by BLI (Rabinovich et al., 2008). Briefly, packaging cells (293-METR) were plated on T125 flasks and transfected the following day with pCMV R8.2, VSV-G, and pLVU3G-effLuc-T2A-mKateS158A (FIG. 19) plasmids in conjunction with Lipofectamine 2000 transfection reagent according to manufacturer's instructions (Invitrogen). Viral particles were harvested 48 and 72 h post-transfection and concentrated through 100 kDa NMWL filters (cat #UFC810096, Milli-Pore, Billerica, Mass.). CAOV3 cells were plated in a 6-well plate and the following day virus coding for effLuc-mKate was added with 8 μg/mL polybrene. Plate was spun at 1,800 rpm for 1.5 h and 6 h later the viral-conditioned supernatant was replaced with DMEM complete media, which was changed the following day. Single-cell clones of transduced CAOV3 were derived by limiting dilution that displayed the same morphology as the parental cell line and clone 1C2 was chosen as it had uniform mKate fluorescence with high (>10$^6$ signal to noise ratio) effLuc activity.

Mouse experiments. In vivo anti-tumor efficacy was assessed in NSG mice (NOD.Cg-Prkdc$^{scid}$Il2rγ$^{tm1Wjl}$/SzJ; Jackson Laboratories). CAOV3-effLuc-mkate (clone 1C2; 3×10$^6$ cells/mouse) tumors were established by intraperitoneal (i.p.) injection and mice were randomly distributed into treatment groups. Eight days later (designated Day 0), a dose escalation regimen was initiated with γδ T cells administered i.p. and PBS administered i.p. as a negative control. T-cell doses were 3×10$^6$, 6×10$^6$, 10$^7$, and 1.5×10$^7$ on days 0, 7, 14, and 21, respectively. Non-invasive BLI was performed during the course of the experiments to serially measure tumor burden of CAOV3-effLuc-mKate following subcutaneous administration of D-Luciferin (cat #122796, Caliper, Hopkinton, Mass.) as detected with IVIS®-100 Imager (Caliper). BLI was analyzed using LIVING IMAGE® software (version 2.50, Xenogen, Caliper).

TABLE 1

Antibodies used.

| Antibody specificity | Clone | Vendor |
|---|---|---|
| CD3 | SK7 | BD Biosciences |
| CD4 | RPA-T4 | BD Biosciences |
| CD8 | RPA-T8 | BD Biosciences |
| CD19 | HIB19 | BD Biosciences |
| CD25 | M-A251 | BD Biosciences |
| CD27 | M-T271 | BD Biosciences |
| CD28 | L293 | BD Biosciences |
| CD32 | FLI8.26 (2003) | BD Biosciences |
| CD38 | HB7 | BD Biosciences |
| CD45RA | HI100 | BD Biosciences |
| CD45RO | UCHL1 | BD Biosciences |
| CD56 | B159 | BD Biosciences |
| CD57 | NK-1 | BD Biosciences |
| CD62L | Dreg 56 | BD Biosciences |
| CD64 | 10.1 | BD Biosciences |
| CD86 | 2331 FUN-1 | BD Biosciences |
| CD95 | DX2 | BD Biosciences |
| CD122 | TM-Beta 1 | BD Biosciences |
| CD127 | HIL-7R-M21 | BD Biosciences |
| CD137L | C65-485 | BD Biosciences |
| CCR7 | TG8 | eBiosciences |
| CXCR4 | 12G5 | BD Biosciences |
| CLA | HECA-452 | BD Biosciences |
| CCR4 | 1G1 | BD Biosciences |
| ICOS | ISA-3 | eBiosciences |
| PD-1 | MIH4 | BD Biosciences |
| TCRαβ | WT31 | BD Biosciences |
| TCRγδ | B1 | BD Biosciences |
| TCRγδ | IMMU510 | Thermo Fisher |
| TCRδ1 | TS-1 | Thermo/Pierce |
| TCRδ2 | B6 | BD Biosciences |
| TCRγ9 | B3 | BD Biosciences |
| NMS | 015-000-120 | Jackson ImmunoResearch |
| DNAM1 | DX11 | BD Biosciences |
| NKG2D | 1D11 | BD Biosciences |
| IL15 | 34559 | R&D Systems |
| IFNγ | 4S.B3 | BD Biosciences |

Example 3—Discussion

This study establishes aAPC clone #4 as a cellular platform for the sustained proliferation of multiple populations of γδ T cells that retain broad reactivity against hematologic malignancies and solid tumors. T cells expressing certain Vδ TCR usage have been associated with clinical responses against cancer. For example, Vδ1 T cells have not been directly infused for therapy. The inventors' data establish that these cells could mediate anti-tumor immunity and support the adoptive transfer of Vδ1 T cells for cancer therapy. The inventors' propagated/activated Vδ2 T cells exhibited the highest killing of tumor cells and cytokine production. A role for Vδ1$^{neg}$Vδ2$^{neg}$-T cells in targeting tumors was previously unknown; however, the inventors' results directly show that Vδ1$^{neg}$Vδ2$^{neg}$ cells exhibit anti-tumor activity, and this subset could also be of benefit to immunocompromised patients. In aggregate, the data herein lend impetus to adoptive transfer of γδ T cells that maintain expression of all Vδ TCR types as a treatment for tumors and opportunistic viral infections.

Engineered aAPC can be used to generate large numbers of γδ T cells that maintain polyclonal TCR repertoire and have an ability to kill tumors, but not normal cells. The approach to infusing polyclonal γδ T cells is further supported by the ability to of aAPC generate $T_N$, $T_{CM}$, and $T_{EM}$ γδ T cells that exhibit a range of effector functions including production of pro-inflammatory cytokines and exerting direct cytotoxicity against tumors in vitro and in vivo. Clone #4 has been produced as a master cell bank in compliance with current good manufacturing practice (cGMP) and provides a clear path to generating clinical-grade γδ T cells for human application. Clinical trials can now, for the first time, test the efficacy of adoptive transfer of T cells maintaining a polyclonal repertoire of TCRγδ therapy for both solid and hematological tumors with the potential to treat infection.

Example 4—Alternative Protocol for the Isolation and Propagation of γδ T Cells

Alternative γδ T Cell Isolation Procedure.

Figure 20:
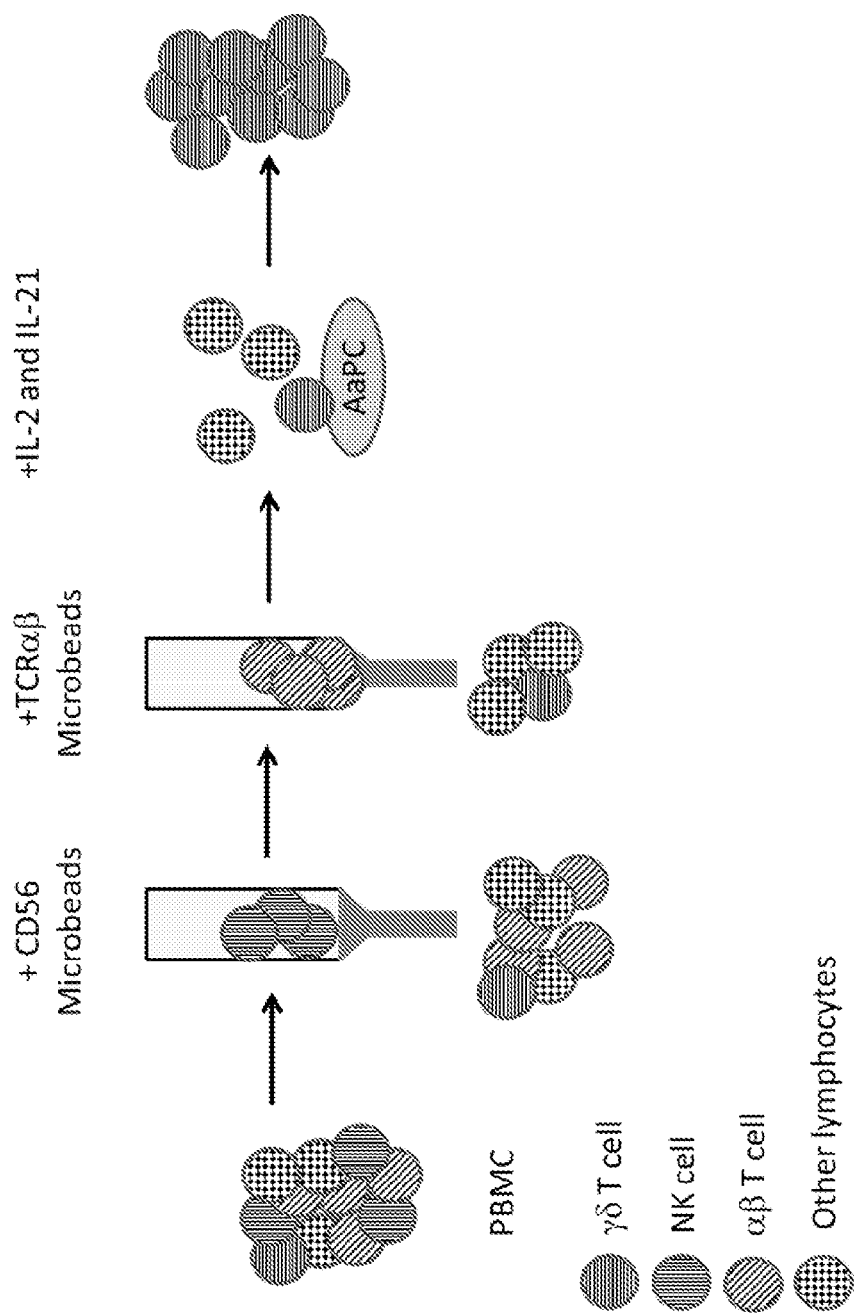
FIG. 20. Alternative protocol for the isolation and propagation of γδ T cells. First, CD56$^+$ NK cells and TCRαβ$^+$ αβ T cells are first extracted using microbeads. The remaining cells are incubated in the presence of aAPC to selective promote the propagation and expansion of the γδ T cell population.

Peripheral blood mononuclear cells (PBMC) from patient buffy coats were depleted of CD56$^+$ Natural Killer (NK) cells and αβ T cells by incubating with paramagnetic microbeads and running through successive columns consisting of ferromagnetic spheres (Miltenyi) in the presence of a magnetic field. The remaining cells, which contain γδ T cells among more numerous lymphocyte populations, are cultured on modified K562 activating and propagating cells (aAPC) in the presence of IL-2 and IL-21, resulting in the selective expansion of γδ T cells (see FIG. 20).

This method of isolation is advantageous as both CD56 beads and TCRαβ beads are available as clinical-grade reagents. The proposed expansion protocol (using aAPC in the presence of IL-2 and IL-21) is the same.

Figure 21:
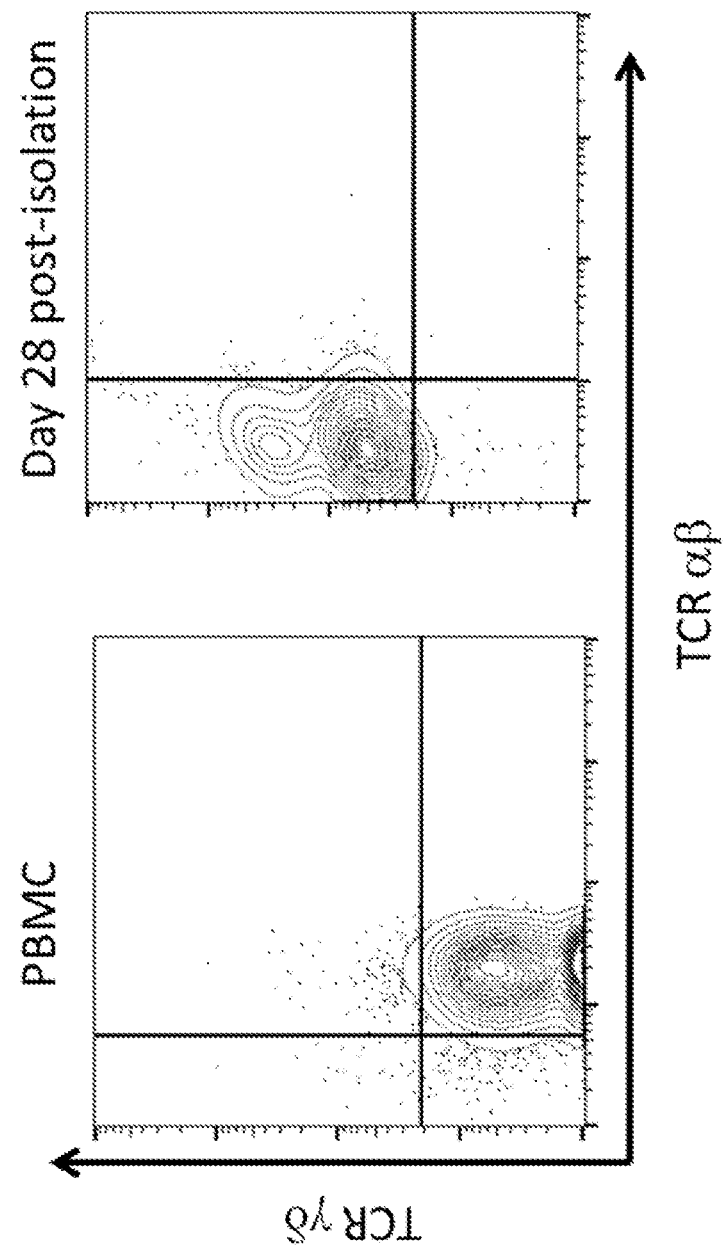
FIG. 21. Expansion of γδ T cells. CD3$^+$ T cells from fresh donor PBMC are shown (left panel) and compared to cells after expansion using the alternative isolation protocol (right panel).

CD3$^+$ T cells from fresh donor PBMC were compared to cells after expansion using the modified isolation protocol. Initially, γδ T cells are a minority population in the peripheral blood. Depletion of NK cells and αβ T cells followed by propagation on aAPC allowed for the expansion of γδ T cells (FIG. 21).

Figure 22:
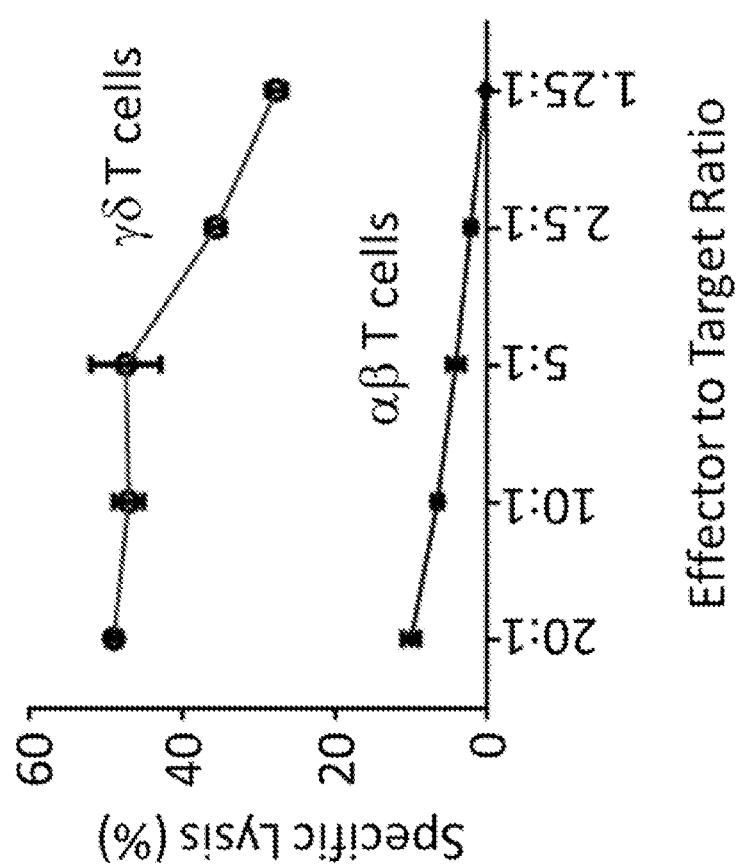
FIG. 22. Specific lysis of pancreatic cancer cell line 10.05 by γδ and αβ T cells. Standard 4-h CRA was performed with increasing effector (polyclonal γδ T cells) to target (E:T) ratios against a pancreatic cancer cell line. Data are mean±SD (n=3 wells per assay) from two independent experiments.

The specific lysis of a pancreatic cancer cell line by γδ T cells expanded from PBMC following successive depletions of CD56$^+$ and TCRαβ$^+$ cells is shown in FIG. 22. γδ T cells exhibited inherent activity against a pancreatic cancer cell line, while αβ T cells did not.

Example 5—Further Alternative Protocols for the Propagation of γδ T Cells

γδ T cells will be triggered using different anti-CD3 antibody clones leading to distinct outcomes (Dopfer et al., 2014). For example, clone OKT3 can be used to induce cytokine production from γδ T cells and clone UCHT1 can be used to induce greater cytotoxicity against target cells.

γδ T cells will also be propagated on either aAPC loaded with OKT3, UCHT1, or both antibodies in the presence of IL-2 and IL-21; or on microbeads loaded with OKT3, UCHT1, or both antibodies in the presence of IL-2 and IL-21.

The effectiveness of γδ T cells in combating various cancer cell lines and primary cancers in vitro and in vivo will be tested following the various expansion mechanisms.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,690,915
U.S. Pat. No. 6,225,042
U.S. Pat. No. 6,355,479
U.S. Pat. No. 6,362,001
U.S. Pat. No. 6,410,319
U.S. Pat. No. 6,790,662
U.S. Pat. No. 7,109,304
U.S. Patent Application Publication No. 2009/0017000
U.S. Patent Application Publication No. 2009/0004142
PCT Publication No. WO2007/103009
Bauer et al., Activation of NK cells and T cells by NKG2D, a receptor for stress-inducible MICA. *Science*, 285:727-729, 1999.
Boismenu and Havran, An innate view of γδ T cells. *Curr. Op. Immunol.*, 9:57, 1997.
Bonneville et al., Gammadelta T cell effector functions: a blend of innate programming and acquired plasticity. *Nature Reviews. Immunology*, 10:467-478, 2010.
Bukowski et al., Recognition and destruction of virus-infected cells by human γδ CTL. *J. Immunol.*, 153:5133, 1994.
Caccamo et al., Differentiation, phenotype, and function of interleukin-17-producing human Vgamma9Vdelta2 T cells. *Blood*, 118:129-138, 2011.
Choudhary et al., Selective lysis of autologous tumor cells by recurrent γδ tumor-infiltrating lymphocytes from renal carcinoma. *J. Immunol.*, 154:3932, 1995.
D'Asaro et al., V gamma 9V delta 2 T lymphocytes efficiently recognize and kill zoledronate-sensitized, imatinib-sensitive, and imatinib-resistant chronic myelogenous leukemia cells. *Journal of Immunology*, 184:3260-3268, 2010.
Denman et al., Membrane-bound IL-21 promotes sustained ex vivo proliferation of human natural killer cells. *PloS One*, 7:e30264, 2012.
Dokouhaki et al., Adoptive immunotherapy of cancer using ex vivo expanded human gammadelta T cells: A new approach. *Cancer Letters*, 297:126-136, 2010.
Dopfer et al., The CD3 conformational change in the γδ T cell receptor is not triggered by antigens but can be enforced to enhance tumor killing. *Cell Reports*, 7:1704-1715, 2014.
Elloso et al., Human gamma delta T cell subset-proliferative response to malarial antigen in vitro depends on CD4+ T cells or cytokines that signal through components of the IL-2R. *J. Immunol.*, 157:2096, 1996.
Gilfillan et al., DNAM-1 promotes activation of cytotoxic lymphocytes by nonprofessional antigen-presenting cells and tumors. *The Journal of Experimental Medicine*, 205: 2965-2973, 2008.
Godder et al., Long term disease-free survival in acute leukemia patients recovering with increased gammadelta T cells after partially mismatched related donor bone marrow transplantation. *Bone Marrow Transplant*, 39:751-757, 2007.
June, Principles of adoptive T cell cancer therapy. *The Journal of Clinical Investigation*, 117:1204-1212, 2007.
Kabelitz et al., Perspectives of gammadelta T cells in tumor immunology. *Cancer Research*, 67:5-8, 2007.
Kang et al., Adoptive immunotherapy of lung cancer with immobilized anti-TCRgammadelta antibody-expanded human gammadelta T-cells in peripheral blood. *Cancer Biology & Therapy*, 8:1540-1549, 2009.
Kim et al., *Nature*, 22(4):403-410, 2004.
Kitayama et al., Functional analysis of TCRγδ4" T cells in tumour-infiltrating lymphocytes (TIL) of human pancreatic cancer. *Clin. Exp. Immunol.*, 93:442, 1993.
Kondo et al., Zoledronate facilitates large-scale ex vivo expansion of functional gammadelta T cells from cancer patients for use in adoptive immunotherapy. *Cytotherapy*, 10:842-856, 2008.
Lamb et al., Influence of T cell depletion method on circulating gammadelta T cell reconstitution and potential role in the graft-versus-leukemia effect. *Cytotherapy*, 1:7-19, 1999.
Lamb et al., Increased frequency of TCR gamma delta+T cells in disease-free survivors following T cell-depleted, partially mismatched, related donor bone marrow transplantation for leukemia. *J. Hematother.*, 5:503-509, 1996.
Lamb et al., Human gammadelta(+) T lymphocytes have in vitro graft vs leukemia activity in the absence of an allogeneic response. *Bone Marrow Transplant*, 27:601-606, 2001.
Lang et al., *J. Immunol.*, 154:5986, 1995.
Lang et al., Pilot trial of interleukin-2 and zoledronic acid to augment gammadelta T cells as treatment for patients with refractory renal cell carcinoma. *Cancer Immunology, Immunotherapy: CII*, 60:1447-1460, 2011.
Lefranc et al., Nomenclature of the human T cell receptor genes. *Curr. Protoc. Immunol.*, 40(A.1O):1-23, 2001.
Lopez et al., CD2-mediated IL-12-dependent signals render human gamma delta-T cells resistant to mitogen-induced apoptosis, permitting the large-scale ex vivo expansion of functionally distinct lymphocytes: implications for the development of adoptive immunotherapy strategies. *Blood*, 96:3827-3837, 2000.
Manuri et al., piggyBac transposon/transposase system to generate CD19-specific T cells for the treatment of B-lineage malignancies. *Human Gene Therapy*, 21:427-437, 2010.
Maus et al., Ex vivo expansion of polyclonal and antigen-specific cytotoxic T lymphocytes by artificial APCs expressing ligands for the T-cell receptor, CD28 and 4-1BB. *Nature Biotechnology*, 20:143-148, 2002.

Nagamine et al., Induction of gamma delta T cells using zoledronate plus interleukin-2 in patients with metastatic cancer. Hiroshima *J. Med. Sci.*, 58:37-44, 2009.

Nicol et al., Clinical evaluation of autologous gamma delta T cell-based immunotherapy for metastatic solid tumours. *British Journal of Cancer*, 105:778-786, 2011.

Numbenjapon et al., Characterization of an artificial antigen-presenting cell to propagate cytolytic CD19-specific T cells. *Leukemia*, 20:1889-1892, 2006.

Pang et al., Understanding the complexity of gammadelta T-cell subsets in mouse and human. *Immunology*, 136:283-290, 2012.

Rabinovich et al., Visualizing fewer than 10 mouse T cells with an enhanced firefly luciferase in immunocompetent mouse models of cancer. *Proceedings of the National Academy of Sciences USA*, 105:14342-14346, 2008.

Rostene et al., Chemokines: a new class of neuromodulator? *Nat. Rev. Neurosci.*, 8:895-903, 2007.

Singh et al., Reprogramming CD19-Specific T Cells with IL-21 Signaling Can Improve Adoptive Immunotherapy of B-Lineage Malignancies. *Cancer Research*, 71:3516-3527, 2011.

Singh et al., Manufacture of Clinical-Grade CD19-Specific T Cells Stably Expressing Chimeric Antigen Receptor Using Sleeping Beauty System and Artificial Antigen Presenting Cells. *PLoS One*, 8:e64138, 2013.

Singh et al., Redirecting specificity of T-cell populations for CD19 using the Sleeping Beauty system. *Cancer Research*, 68:2961-2971, 2008.

Stresing et al., Bisphosphonates in cancer therapy. *Cancer Letters*, 257:16-35, 2007.

Suhoski et al., Engineering artificial antigen-presenting cells to express a diverse array of co-stimulatory molecules. *Molecular Therapy: The Journal of the American Society of Gene Therapy*, 15:981-988, 2007.

Thompson et al., Activation of gammadelta T cells by bisphosphonates. *Advances in Experimental Medicine and Biology*, 658:11-20, 2010.

Topalian and Rosenberg, Therapy of cancer using the adoptive transfer of activated killer cells and interleukin-2. *Acta Haematol.*, 78(Suppl. 1):75-76, 1987.

Turchinovich and Pennington, T cell receptor signalling in gammadelta cell development: strength isn't everything. *Trends in Immunology*, 32:567-573, 2011.

Turkman et al., Fluorinated cannabinoid CB2 receptor ligands: synthesis and in vitro binding characteristics of 2-oxoquinoline derivatives. *Bioorg. Med. Chem.*, 19:5698-5707, 2011.

Wallace et al., Gamma/delta T lymphocytes in viral infections. *J. Leuk. Biol.*, 58:277, 1995.

Wilhelm et al., Gammadelta T cells for immune therapy of patients with lymphoid malignancies. *Blood*, 102:200-206, 2003.

Xu et al., Crystal structure of a gammadelta T-cell receptor specific for the human MHC class I homolog MICA. *Proceedings of the National Academy of Sciences USA*, 108:2414-2419, 2011.

Zhang et al., A new approach to simultaneously quantify both TCR alpha- and beta-chain diversity after adoptive immunotherapy. *Clinical Cancer Research: An Official Journal of the American Association for Cancer Research*, 18:4733-4742, 2012.

Zocchi et al., Selective lysis of the autologous tumor by δTCS1+γδ+tumor-infiltrating lymphocytes from human lung carcinomas. *Eur. J Immunol.*, 20:2685, 1990.

The invention claimed is:

1. A method of expanding γδ T cells to sufficient numbers for use in therapy comprising:
   (a) obtaining a sample of cells comprising a first polyclonal γδ T-cell population;
   (b) isolating the first polyclonal γδ T-cell population;
   (c) culturing the first polyclonal γδ T-cell population with artificial antigen presenting cells (aAPCs) in the presence of interleukin-2 (IL-2) and interleukin-21 (IL-21), thereby inducing proliferation of the γδ T cells to sufficient numbers for use in therapy, wherein the aAPCs are engineered K562 cells that express CD137L, CD64, CD86, and mIL15; and
   (d) isolating the cultured γδ T-cells.

2. The method of claim 1, further comprising depleting the sample of cells of CD56- and TCRα-expressing cells.

3. The method of claim 1, wherein the sample of cells is a peripheral blood sample, an umbilical cord blood sample, or a tissue sample.

4. The method of claim 1, wherein the sample of cells is obtained from a single subject.

5. The method of claim 1, wherein the first polyclonal γδ T-cell population comprises about $10^4$ to about $10^6$ γδ T cells.

6. The method of claim 1, wherein culturing the first polyclonal γδ T-cell population with aAPCs comprises culturing the cells at a ratio of about 1:2 (γδ T cells to aAPCs).

7. The method of claim 1, wherein culturing the first polyclonal γδ T-cell population with aAPCs results in at least a 100-fold increase in the number of polyclonal γδ T cells.

\* \* \* \* \*

UNITED STATES PATENT AND TRADEMARK OFFICE
CERTIFICATE OF CORRECTION

PATENT NO. : 9,907,820 B2
APPLICATION NO. : 15/031610
DATED : March 6, 2018
INVENTOR(S) : Laurence J. N. Cooper and Drew C. Deniger It is certified that error appears in the above-identified patent and that said Letters Patent is hereby corrected as shown below:

In the Specification

Column 1, Lines 10-12, delete "The invention was made with government support under Grant No. 10626252 awarded by the Department of Defense. The government has certain rights in the invention." and replace with --This invention was made with government support under grant number W81XWH-11-1-0459 awarded by the U.S. Department of the Army. The government has certain rights in the invention.-- therefor.

Signed and Sealed this
Thirty-first Day of July, 2018

Andrei Iancu
*Director of the United States Patent and Trademark Office*